United States Patent
Dibble et al.

(10) Patent No.: US 11,859,180 B2
(45) Date of Patent: *Jan. 2, 2024

(54) ANTISENSE OLIGONUCLEOTIDE COMPOSITIONS

(71) Applicant: Ionis Pharmaceuticals, Inc., Carlsbad, CA (US)

(72) Inventors: Andrew Dibble, Vlsta, CA (US); Lloyd Tillman, Encinitas, CA (US); Bret Coldren, Vista, CA (US); Marc Lim, Fullerton, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/896,752

(22) Filed: Jun. 9, 2020

(65) Prior Publication Data

US 2021/0079391 A1    Mar. 18, 2021

Related U.S. Application Data

(63) Continuation of application No. 16/203,156, filed on Nov. 28, 2018, now abandoned, which is a continuation of application No. 15/293,613, filed on Oct. 14, 2016, now Pat. No. 10,174,318, which is a continuation of application No. 14/401,761, filed as application No. PCT/US2013/041701 on May 17, 2013, now abandoned.

(60) Provisional application No. 61/648,556, filed on May 17, 2012.

(51) Int. Cl.
  *C12N 15/113* (2010.01)
  *C12N 15/11* (2006.01)
  *A61K 31/7115* (2006.01)
  *A61K 31/712* (2006.01)
  *A61K 31/7125* (2006.01)
  *C07H 21/04* (2006.01)

(52) U.S. Cl.
  CPC .......... *C12N 15/113* (2013.01); *A61K 31/712* (2013.01); *A61K 31/7115* (2013.01); *A61K 31/7125* (2013.01); *C12N 15/111* (2013.01); *C12N 2310/11* (2013.01); *C12N 2310/315* (2013.01); *C12N 2310/321* (2013.01); *C12N 2310/323* (2013.01); *C12N 2310/3231* (2013.01); *C12N 2310/3341* (2013.01); *C12N 2310/3525* (2013.01); *C12N 2320/50* (2013.01); *C12N 2320/51* (2013.01); *C12N 2320/52* (2013.01)

(58) Field of Classification Search
  None
  See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,374,527 A | 12/1994 | Grossman |
| 5,432,272 A | 7/1995 | Benner |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,721,138 A | 2/1998 | Lawn |
| 5,750,692 A | 5/1998 | Cook et al. |

(Continued)

FOREIGN PATENT DOCUMENTS

| | | |
|---|---|---|
| EP | 2316968 | 5/2011 |
| EP | 2021472 | 6/2011 |

(Continued)

OTHER PUBLICATIONS

Agrawal et al., "Antisense oligonucleotides: towards clinical trials" TIBTECH (1996) 14:376-387.

(Continued)

*Primary Examiner* — Kimberly Chong
(74) *Attorney, Agent, or Firm* — Knobbe, Martens, Olson & Bear, LLP

(57) ABSTRACT

The present disclosure provides compositions comprising an antisense oligonucleotide and one or more excipients that modulates viscosity, turbidity or both viscosity and turbidity. In certain embodiments, compositions comprising an antisense oligonucleotide and one or more excipients having low viscosity are provided. In certain embodiments, compositions comprising an antisense oligonucleotide and one or more excipients having low turbidity are provided. In certain embodiments, pharmaceutical compositions comprising an antisense oligonucleotide and one or more excipients having low viscosity and turbidity are provided.

20 Claims, 2 Drawing Sheets

Specification includes a Sequence Listing.

(56) References Cited

U.S. PATENT DOCUMENTS

| | | |
|---|---|---|
| 5,763,588 A | 6/1998 | Matteucci et al. |
| 5,801,154 A | 9/1998 | Baracchini et al. |
| 5,830,653 A | 11/1998 | Froehler et al. |
| 5,866,551 A | 2/1999 | Benoit et al. |
| 5,877,022 A | 3/1999 | Stinchcomb et al. |
| 6,005,096 A | 12/1999 | Matteucci et al. |
| 6,008,344 A | 12/1999 | Bennett et al. |
| 6,080,580 A | 6/2000 | Baker et al. |
| 6,268,490 B1 | 7/2001 | Imanishi et al. |
| 6,512,161 B1 | 1/2003 | Rouy et al. |
| 6,515,191 B2 | 2/2003 | Lal et al. |
| 6,525,191 B1 | 2/2003 | Ramasamy |
| 6,573,050 B1 | 6/2003 | Ben-David et al. |
| 6,582,908 B2 | 6/2003 | Fodor et al. |
| 6,613,567 B1 | 9/2003 | Bennett et al. |
| 6,670,461 B1 | 12/2003 | Wengel et al. |
| 6,764,822 B1 | 7/2004 | Butler et al. |
| 6,770,748 B2 | 8/2004 | Imanishi et al. |
| 6,794,499 B2 | 9/2004 | Wengel et al. |
| 6,809,193 B2 | 10/2004 | McKay et al. |
| 7,034,133 B2 | 4/2006 | Wengel et al. |
| 7,053,207 B2 | 5/2006 | Wengel |
| 7,227,014 B2 | 6/2007 | Crooke et al. |
| 7,259,150 B2 | 8/2007 | Crooke et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,723,508 B2 | 5/2010 | Crooke et al. |
| 7,741,305 B2 | 6/2010 | Crooke et al. |
| 7,741,457 B2 | 6/2010 | Seth et al. |
| 8,138,328 B2 | 3/2012 | Crooke et al. |
| 8,673,632 B2 | 3/2014 | Crooke et al. |
| 9,574,193 B2 | 2/2017 | Crooke et al. |
| 9,884,072 B2 | 2/2018 | Crooke et al. |
| 9,885,045 B2 | 2/2018 | Crooke et al. |
| 9,957,504 B2 | 5/2018 | Prakash et al. |
| 10,174,318 B2 | 1/2019 | Dibble et al. |
| 10,472,629 B2 | 11/2019 | Crooke et al. |
| 10,478,448 B2 | 11/2019 | Crooke et al. |
| 11,634,711 B2 | 4/2023 | Crooke et al. |
| 2001/0053519 A1 | 12/2001 | Fodor et al. |
| 2003/0104410 A1 | 6/2003 | Mittman |
| 2003/0119766 A1 | 6/2003 | Crooke et al. |
| 2003/0165948 A1 | 9/2003 | Alsmadi et al. |
| 2003/0228597 A1 | 12/2003 | Cowsert et al. |
| 2004/0171570 A1 | 9/2004 | Allerson et al. |
| 2004/0242516 A1 | 12/2004 | Crooke |
| 2005/0026169 A1 | 2/2005 | Cargill et al. |
| 2005/0130923 A1 | 6/2005 | Bhat et al. |
| 2005/0244851 A1 | 11/2005 | Blume et al. |
| 2006/0281698 A1 | 12/2006 | Crooke et al. |
| 2007/0031844 A1 | 2/2007 | Khvorova et al. |
| 2007/0110757 A1 | 5/2007 | Wei et al. |
| 2007/0287831 A1 | 12/2007 | Seth et al. |
| 2008/0039618 A1 | 2/2008 | Allerson et al. |
| 2009/0012281 A1 | 1/2009 | Swayze et al. |
| 2009/0318536 A1 | 12/2009 | Isis et al. |
| 2010/0035983 A1 | 2/2010 | Celera et al. |
| 2010/0197762 A1 | 8/2010 | Swayze |
| 2011/0039910 A1 | 2/2011 | Crooke et al. |
| 2011/0044977 A1 | 2/2011 | Adler et al. |
| 2011/0098343 A1 | 4/2011 | Hayes et al. |
| 2011/0251130 A1 | 10/2011 | Robertson et al. |
| 2011/0294868 A1 | 12/2011 | Monia et al. |
| 2011/0313019 A1 | 12/2011 | Swayze et al. |
| 2012/0316219 A1 | 12/2012 | Crooke et al. |
| 2013/0177468 A1 | 11/2013 | Crooke et al. |
| 2014/0206750 A1 | 7/2014 | Crooke et al. |
| 2015/0126720 A1 | 5/2015 | Prakash et al. |
| 2015/0152411 A1 | 6/2015 | Crooke et al. |
| 2015/0184156 A1 | 7/2015 | Crooke et al. |
| 2015/0337303 A1 | 11/2015 | Crooke et al. |
| 2016/0002624 A1 | 1/2016 | Dibble et al. |
| 2017/0121710 A1 | 5/2017 | Crooke et al. |
| 2017/0182084 A1 | 6/2017 | Crooke et al. |
| 2017/0211062 A1 | 7/2017 | Dibble et al. |
| 2018/0237776 A1 | 8/2018 | Crooke et al. |
| 2018/0256629 A1 | 9/2018 | Crooke et al. |
| 2019/0316123 A1 | 10/2019 | Dibble et al. |
| 2020/0276224 A1 | 9/2020 | Crooke et al. |
| 2021/0002643 A1 | 1/2021 | Crooke et al. |

FOREIGN PATENT DOCUMENTS

| | | |
|---|---|---|
| WO | WO 1996/09392 | 3/1996 |
| WO | WO 1997/17371 | 5/1997 |
| WO | WO 1998/039352 | 9/1998 |
| WO | WO 1999/014226 | 3/1999 |
| WO | WO 1999/34016 | 7/1999 |
| WO | WO 1999/35241 | 7/1999 |
| WO | WO 2003/004602 | 1/2003 |
| WO | WO 2003/014307 | 2/2003 |
| WO | WO 2003/014397 | 2/2003 |
| WO | WO 2004/031237 | 4/2004 |
| WO | WO 2004/094636 | 11/2004 |
| WO | WO 2004/106356 | 12/2004 |
| WO | WO 2004/108916 | 12/2004 |
| WO | WO 2005/000201 | 1/2005 |
| WO | WO 2005/021570 | 3/2005 |
| WO | WO 2005/060542 | 7/2005 |
| WO | WO 2006/060649 | 6/2006 |
| WO | WO 2007/134181 | 11/2007 |
| WO | WO 2007/146511 | 12/2007 |
| WO | WO 2008/098129 | 8/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/073809 | 6/2009 |
| WO | WO 2009/100320 | 8/2009 |
| WO | WO 2010/006215 | 1/2010 |
| WO | WO 2010/036698 | 4/2010 |
| WO | WO 2011/005765 | 1/2011 |
| WO | WO 2011/017521 | 2/2011 |
| WO | WO 2012/037254 | 3/2012 |
| WO | WO 2012/177784 | 12/2012 |
| WO | WO 2013/173789 | 11/2013 |
| WO | WO 2013/177468 | 11/2013 |
| WO | WO 2014/179625 | 11/2014 |
| WO | WO 2017/079739 | 5/2017 |
| WO | WO 2017/079745 | 5/2017 |

OTHER PUBLICATIONS

Albaek et al., "Analogues of a Locked Nucleic Acid with Three-Carbon 2′,4′-Linkages: Synthesis by Ring-Closing Metathesis and Influence of Nucleic Acid Duplex Stability" J. Org. Chem. (2006) 71:7731-7740.

Anderson et al., "A comparison of selected mRNA and protein abundances in human liver" Electrophoresis (1997) 18:533-537.

Altmann et al., "Second Generation Antisense Oligonucleotides—Inhibition of PKC-α and c-raf Kinase Expression by Chimeric Oligonucleotides Incorporating 6″-Substituted Carbocyclic Nucleosides and 2″-O-Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals " Chimia. (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2′-O-(2-Methoxy )ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

(56) References Cited

OTHER PUBLICATIONS

Berg et al. "Spontaneous Atherosclerosis in the Proximal Aorta of LPA Transgenic Mice on a Normal Diet," Atherosclerosis (2002) vol. 163:99-104.
Bergmark et al., "A novel function of lipoprotein [a] as a preferential carrier of oxidized phospholipids in human plasma" J. Lipid Res. (2008) 49(10)2230-2239.
Braasch et al., "Locked nucleic acid (LNA): fine-tuning the recognition of DNA and RNA" Chem. Biol. (2001) 8:1-7.
Braasch et al., "Novel antisense and peptide nucleic acid strategies for controlling gene expression" Biochemistry (2002) 41(14):4503-4510.
Branch et al., "A good antisense molecule is hard to find," TIBS (1998) 23:45-50.
Callow et al., "Expression of human apolipoprotein B and assembly of lipoprotein (a) in transgenic mice" PNAS (1994) 91:2130-2134.
Chiesa et al., "Reconstitution of Lipoprotein (a) by Infusion of Human Low Density Lipoprotein into Transgenic Mice Expressing Human Apolipoprotein (a)" J. of Biological Chem. (1992) 267:24369-24374.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Clarke et al., "Genetic variants associated with Lp(a) lipoprotein level and coronary disease" N. Engl. J. Med. (2009) 361(26):2518-2528.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Deverre et al., "A competitive enzyme hybridization assay for plasma determination of phosphodiester and phosphorothioate antisense oligonucleotides" Nucleic Acids Res. (1997) 25:3584-3589.
Dias et al., "Potential roles of antisense oligonucleotides in cancer therapy. The example of bcl-2 antisense oligonucleotides." European J. of Pharmaceutics and Biopharmaceutics (2002) 54:263-269.
Elayadi et al., "Application of PNA and LNA oligomers to chemotherapy" Curr. Opinion Invens. Drugs (2001) 2:558-561.
Elbashir et al., "Functional anatomy of siRNAs for mediating efficient RNAi in *Drosophila melanogaster* embryo lysate" The EMBO Journal (2001) 20(23):6877-6888.
Englisch et al., "Chemically Modified Oligonucleotides as Probes and Inhibitors" Agnew Chem. Int. Ed. Engl. (1991) 30:613-629.
Erqou et al., "Lipoprotein(a) concentration and the risk of coronary heart disease, stroke, and nonvascular mortality" JAMA. (2009) 302(4):412-423.
Expert Panel on Detection, Evaluation, and Treatment of High Blood Cholesterol in Adults, "Executive Summary of the Third Report of the National Cholesterol Education Program (NCEP) Expert Panel on Detection, Evaluation, and Treatment of High Blood Cholesterol in Adults (Adult Treatment Panel III)" JAMA (2001) 285(19):2486-2497.
Frazer et al., "The apolipoprotein(a) gene is regulated by sex hormones and acute-phase inducers in YAC transgenic mice" Nat. Genet. (1995) 9(4):424-431.
Frank et al., "Adenovirus-mediated apo(a)-antisense-RNA expression efficiently inhibits apo(a) synthesis in vitro and in vivo" Gene Therapy (2001) 8:425-430.
Frank et al., "The apolipoprotein (a) gene resides on human chromosome 6q26-27, in close proximity to the homologous gene for plasminogen" Hum. Genet. (1988) 79:352-356.
Fredrickson et al., "A system for phenotyping hyperlipoproteinemia" Circulation (1965) 31:321-327.
Fredrickson et al., "Fat transport in lipoproteins—an integrated approach to mechanisms and disorders" N. Engl. J. Med. (1967) 276(1):34-42.

Freer et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fritz et al., "Cationic Polystyrene Nonoparticles: Preparation and Characterization of a Model Drug Carrier System for Antisense Oligonucleotides" Journal of Colloid and Interface Science (1997) 195:272-288.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
Geary et al., "A nonradioisotope biomedical assay for intact oligonucleotide and its chain-shortened metabolites used for determination of exposure and elimination half-life of antisense drugs in tissue" Anal. Biochem. (1999) 274(2):241-248.
Gewirtz et al., "Facilitating oligonucleotide delivery: Helping antisense deliver on its promise" PNAS (1996) 93:3161-3163.
Graham et al., "Antisense inhibition of apolipoprotein(a) in cynomolgus monkeys significantly reduces plasma apolipoprotein(a) levels without affecting plasminogen or other major lipid classes" Circulation (2012) 126(21): abstract A11050.
Graham et al., "Antisense inhibition of apolipoprotein(a) in cynomolgus monkeys significantly reduces plasma apolipoprotein(a) levels without affecting plasminogen or other major lipid classes" Powerpoint presentation from American Hearth Association(AHA) 2012 Scientific Sessions, presented Nov. 5, 2012.
Grainger et al., "Activation of transforming growth factor-beta is inhibited in transgenic apolipoprotein (a) mice" Nature (1994) 370:460-462.
Green et al., "Antisense Oligonucleotides: An Evolving Technology for the Modulation of Gene Expression in Human Disease" J. Am. Coll. Surg. (2000) 191:93-105.
Hajjar et al., "The role of lipoprotein (a) in atherogenesis and thrombosis" Annu. Rev. Med. (1996) 47:423-442.
Holen et al., "Positional effects of short interfering RNAs targeting the human coagulation trigger Tissue Factor" Nucleic Acids Research (2002) 30(8):1757-1766.
International Search Report for application PCT/US2013/042532 dated Dec. 6, 2013.
International Search Report for application PCT/US2013/041701 dated Nov. 12, 2013.
Jen, "Suppression of Gene Expression by Targeted Disruption of Messenger RNA: Available Options and Current Strategies" Stem Cells (2000) 18:307-319.
Jones et al., "RNA quantitation by fluorescence-based solution assay: RiboGreen reagent characterization" Anal. Biochem. (1998) 265(2):368-374.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Kamstrup et al., "Extreme lipoprotein(a) levels and risk of myocardial infarction in the general population: the Copenhagen City Heart Study" Circulation (2008) 117(2):176-184.
Katan et al., "Characteristics of human hypo- and hyperresponders to dietary cholesterol" Am. J. Epidemiol. (1987) 125:387-399.
Koornneef et al., "Apolipoprotein B knockdown by AAV-delivered shRNA lowers plasma cholesterol in mice" Mol. Ther. (2011) 19(4):731-740.
Koschinsky, Marlys L., "Lipoprotein(A): On the Cutting Edge of Occam's Razor, website." 8 pages, Jun. 2004.
Koschinsky et al., "Structure-function relationships in apolipoprotein(a): insights into lipoprotein(a) assembly and pathogenicity" Curr. Opin. Lipidol. (2004) 15(2):167-174.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kostner et al., "Lipoprotein (a): Still an Enigma?" Current Opinion in Lipidology (2002) 13:391-396.

(56) References Cited

OTHER PUBLICATIONS

Kraft et al., "Frequency distributions of apolipoprotein(a) kringle IV repeat alleles and their effects on lipoprotein(a) levels in Caucasian, Asian, and African populations: the distribution of null alleles is non-random" Eur. J. Hum. Genet. (1996) 4(2):74-87.

Kumar et al., "The first analogues of LNA (locked nucleic acids): phosphorothioate-LNA and 2'-thio-LNA" Bioorg Med Chem Lett. (1998) 8:2219-2222.

Lawn et al., "Atherogenesis in transgenic mice expressing human apolipoprotein (a)" Nature (1992) 360:670-672.

Leeds et al., "Quantitation of phosphorothioate oligonucleotides in human plasma" Anal. Biochem. (1996) 235(1):36-43.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann et al., "DNA Analogues: From Supramolecular Principles to Biological Properties" Bioorganic & Medicinal Chemistry (2002) 10:841-854.

Lippi et al., "Screening and therapeutic management of lipoprotein(a) excess: review of the epidemiological evidence, guidelines and recommendations" Clin. Chim. Acta. (2011) 412(11-12):797-801.

Lippi et al., "Antisense therapy, in the treatment of hypercholesterolemia" European Journal of Internal Medicine (2011) 22(6): 541-546.

Maher et al., "Comparative hybrid arrest by tandem antisense oligodeoxy ribonucleotides or oligodeoxyribonucleoside methylphosphonates in a cell-free system" Nuc. Acid. Res. (1988) 16(8):3341-3358.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Martin, "New acces to 2'-O-alkylated ribonucleosides and properties of 2'-O-alkylated oligoribonucleotides" Helv. Chim. Acta. (1995) 78:486-504.

McLean et al., "cDNA sequence of human apolipoprotein (a) is homologous to plasminogen" Nature (1987) 330:132-137.

Merki et al., "Antisense oligonucleotide lowers plasma levels of apolipoprotein (a) and lipoprotein (a) in transgenic mice" J. Am. Coll. Cardiol. (2011) 57(15):1611-1621.

Milligan et al., "Current Concepts in Antisense Drug Design" J. Medicinal Chemistry (1993) 36: 1923-1927.

Mishra et al., "Improved leishmanicidal effect of phosphorotioate antisense oligonucleotides by LDL-mediated delivery" Biochim. Biophys. Acta (1995) 1264:229-237.

Morishita et al., "Novel therapeutic strategy for atherosclerosis: ribozyme oligonucleotides against apolipoprotein (a) selectively inhibit apolipoprotein (a) but not plasminogen gene expression" Circulation (1998) 98:1898-1904.

New England Biolabs 1998/99 Catalog (cover page and pp. 121 and 284).

Nowak-Gottl et al., "Lipoprotein (a): its role in childhood thromboembolism" Pediatrics (1997) 99:E11.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Ohmichi et al., "The virtues of self-binding: high sequence specificity for RNA cleavage by self-processed hammerhead ribozymes" Nucleic Acids Res. (2000) 28:776-783.

Ole et al., "Analysis of ribosyl-modified, mixed backbone analogs of a bcl-2/bcl-xL antisense oligonucleotide" Biochimica et Biophysica Acta (2002) 1576:101-109.

Opalinski et al., "Nucleic-Acid Therapeutics: Basic Principles and Recent Applications" Nature Reviews (2002) 1:503-514.

Orum et al., "Locked nucleic acids: A promising molecular family for gene-function analysis and antisense drug development" Curr. Opinion Mol. Ther. (2001) 3:239-243.

Prosnyak et al., "Substitution of 2-aminoadenine and 5-methylcytosine for adenine and cytosine in hybridization probes increases the sensitivity of DNA fingerprinting" Genomics (1994) 21:490-494.

Rainwater et al., "Lipoprotein Lp (a): effects of allelic variation at the LPA locus" J. Exp. Zool. (1998) 282:54-61.

Reynolds et al., "Rational siRNA design for RNA interference" Nature Biotechnology (2004) 22(3):326-330.

Rifai et al., "Apolipoprotein(a) size and lipoprotein(a) concentration and future risk of angina pectoris with evidence of severe coronary atherosclerosis in men: The Physicians' Health Study" Clin. Chem. (2004) 50(8):1364-1371.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi et al., "Heterocyclic Base Modifications in Nucleic Acids and Their Applications in Antisense Oligonucleotides" Antisense Research and Applications (1993) pp. 273-288.

Sandkamp et al., "Lipoprotein (a) is an independent risk factor for myocardial infarction at a young age" Clin. Chem. (1990) 36:20-23.

Schultz et al., "Effects of inhibition of interleukin-6 signalling on insulin sensitivity and lipoprotein (a) levels in human subjects with rheumatoid diseases" PLoS One (2010) 5(12):e14328.

Seed et al., "Relation of serum lipoprotein (a) concentration and apolipoprotein (a) phenotype to coronary heart disease in patients with familial hypercholesterolemia" N. Engl. J. Med. (1990) 322:1494-1499.

Shea et al., "Synthesis, hybridization properties and antiviral activity of lipid-oligodeoxy nucleotide conjugates" Nucl. Acids Res. (1990) 18(13):3777-3783.

Singh et al., "LNA (locked nucleic acids): synthesis and high-affinity nucleic acid recognition" Chem. Commun, (1998) 455-456.

Singh et al., "Synthesis of 2'-amino-LNA: A novel conformationally restricted high-affinity oligonucleotide analogue with a handle" J. Org. Chem. (1998) 63: 10035-10039.

Skerra, "Phosphorothioate primers improve the amplification of DNA sequences by DNA polymerase with proofreading activity" Nucleic Acids Res. (1992) 20:3551-3554.

Smith et al., "Comparison of biosequences" Adv. Appl. Math. (1981) 2(4):482-489.

Sohail et al., "Selecting optimal antisense reagents" Advanced Drug Delivery Review (2000) 44(1):23-34.

Solfrizzi et al., "Lipoprotein(a), apolipoprotein E genotype, and risk of Alzheimer's disease" J. Neurol. Neurosurg. Psychiatry (2002) 72(6):732-736.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Tamm et al., "Antisense therapy in oncology: new hope for an old idea?" The Lancet (2001) 358:489-497.

Tsimikas et al., "Relationship of oxidized phospholipids on apolipoprotein B-100 particles to race/ethnicity, apolipoprotein(a) isoform size, and cardiovascular risk factors: results from the Dallas Heart Study" Circulation (2009) 119(13):1711-1719.

Tuschl et al., 2004, "Selection of siRNA Duplexes from the Target mRNA Sequence," The siRNA user guide, (Rev. 5/04), retrieved Apr. 7, 2009, Max Planck Institute for Biophysical Chemistry, (available at) http://www.rockefeller.edu/labheads/tuschl/sirna.html.

U.S.P.T.O. Office Action from U.S. Appl. No. 12/726,286 dated Sep. 19, 2011.

(56) References Cited

OTHER PUBLICATIONS

U.S.P.T.O. Office Action from U.S. Appl. No. 12/726,286 dated Apr. 16, 2012.
U.S.P.T.O. Office Action from U.S. Appl. No. 12/726,286 dated Jun. 6, 2013.
Vessby et al., "Diverging Effects of Cholestyramine on Apolipoprotein B and Lipoprotein Lp (a)" Atherosclerosis (1982) 44:61-71.
Wahlestedt et al., "Potent and nontoxic antisense oligonucleotide containing locked nucleic acids" Proc. Natl. Acad. Sci. USA (2000) 97: 5633-5638.
Weintraub et al., "Antisense RNA and DNA" Scientific American (1990) 40-46.
Woolf et al. "Specificity of antisense oligonucleotides in vivo" PNAS (1992) 89:7305-7309.
Yang et al., "Transforming Growth Factor-B1 Inhibits Human Keratinocyte Proliferation by Upregulation of a Receptor-Type Tyrosine Phosphatase R-PTP-K Gene Expression" Biochem. Biophys. Res. Commun. (1996) 228:807-812.
Yuan et al., "Hypertriglyceridemia: its etiology, effects and treatment" CMAJ. (2007) 176(8):1113-1120.
Zhang et al., "Antisense Inhibition" Methods in Molecular Medicine (2005) 106: 11-34.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Graham et al., "Antisense inhibition of apolipoprotein(a) in cynomolgus monkeys significantly reduces plasma apolipoprotein(a) levels without affecting plasminogen or other major lipid classes" Poster from American Hearth Association(AHA) 2012 Scientific Sessions, presented Nov. 5, 2012.
Tsimikas et al., "Antisense therapy targeting apolipoprotein(a): a randomised, double-blind, placebo-controlled phase 1 study" Lancet (2015) 386: 1472-1483.
Viney et al., "Antisense oligonucleotides targeting apolipoprotein(a) in people with raised lipoprotein(a): two randomised, double-blind, placebo-controlled, dose-ranging trials" Lancet (2016) 388: 2239-2253.

Standard curve conversion for 13-mm sample tubes for 0-1000 NTU

$y = 1.8148x$
$R^2 = 0.9909$

Turbidity and temperature profiles of 220 mg/mL ASO AE over time.

FIG 3
Turbidity vs (approximate) temperature profile of 220 mg/mL ASO AE
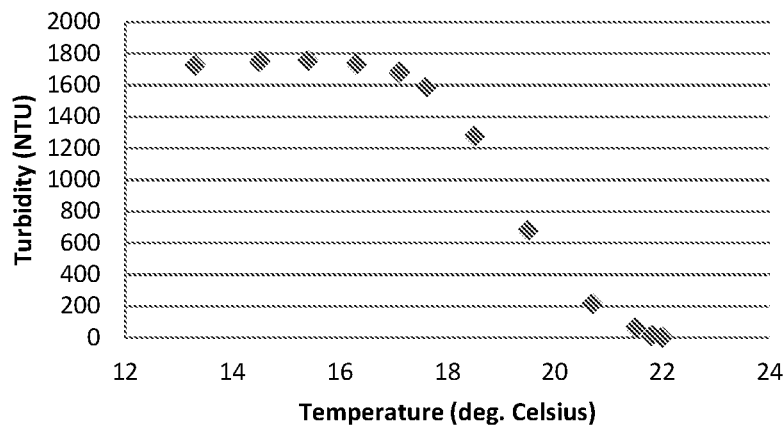
FIG 4
Effect of NTU of Formazin reference suspensions on visible turbidity
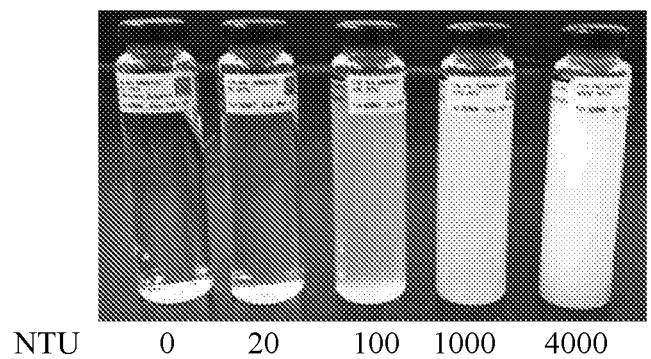
FIG 4A
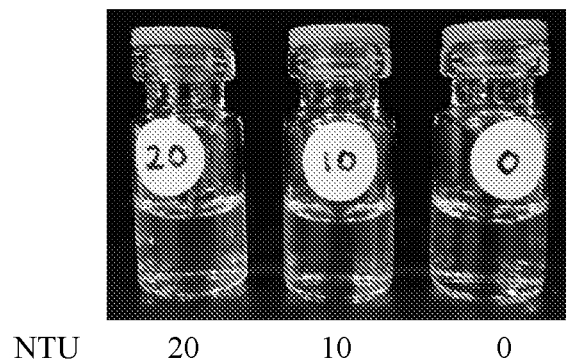
FIG 4B

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
acggcattgg tgcacagttt                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
tcttggttac atgaaatccc                                           20

<210> SEQ ID NO 3
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 3
tgctccgttg gtgcttgttc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ccagctcaac ccttctttaa                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
aatggtttat tccatggcca                                              20

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
ggttcccgag gtgccca                                                 17

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tcacagaatt atcagcagta                                              20

<210> SEQ ID NO 8
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 8
ggacacccac gccccc                                                  16

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 9
tcactttcat aatgctgg                                                18

```
<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gcacactcag caggaccccc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gcctcagtct gcttcgcacc                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
agcatagtta acgagctccc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
agcttcttgt ccagctttat                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
gcagccatgg tgatcaggag                                              20

<210> SEQ ID NO 15
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 15
ctatttggat gtcagc                                                  16

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 16
tgtcatattc ctggatcctt                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
ccgtcgccct tcagcacgca                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tcagggcatt ctttccattc                                              20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
cagcagcaga gtcttcatca t                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gggacgcggc gctcggtcat                                              20

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
gcgtttgctc ttcttcttgc g                                            21

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gcccaagctg gcatccgtca                                              20

<210> SEQ ID NO 23
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 23
ctgagtctgt tttccattct                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gtttgacatg gcacaatgtt                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tcccgcctgt gacatgcatt                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: n = A,T,C or G

<400> SEQUENCE: 26
nnnnnnnnnn nnnnnnnnnn                                          20

<210> SEQ ID NO 27
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: n = A,T,C or G

<400> SEQUENCE: 27
nnnnnnnnnn nnnn                                                14
```

ANTISENSE OLIGONUCLEOTIDE COMPOSITIONS

SEQUENCE LISTING

The present application is being filed along with a Sequence Listing in electronic format. The Sequence Listing is provided as a file entitled CORE0105USC2SEQ.txt, created Nov. 28, 2018, which is 8 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. Certain DNA-like oligomeric compounds have been shown to reduce protein expression. Certain RNA-like compounds are known to inhibit protein expression in cells. Such RNA-like compounds function, at least in part, through the RNA-inducing silencing complex (RISC). RNA-like compounds may be single-stranded or double-stranded. Antisense compounds have also been shown to alter processing of pre-mRNA and to modulate non-coding RNA molecules. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA. Compositions and methods that increase productive uptake of antisense compounds in cells are desired. Compositions and methods that facilitate the manufacture, storage, administration, and delivery of antisense compounds are also desired.

SUMMARY OF THE INVENTION

The present disclosure provides compositions and methods that facilitate the manufacture, storage, administration, and delivery of antisense oligonucleotide solutions. For example, in certain embodiments, the present disclosure provides a number of excipients that reduce the viscosity of an antisense oligonucleotide solution. In certain embodiments, the present disclosure provides a number of excipients that reduce the turbidity of an antisense oligonucleotide solution. In certain embodiments, the present disclosure provides a number of excipients that reduce both the turbidity and the viscosity of an antisense oligonucleotide solution. In certain embodiments, the present disclosure provides a number of excipients that modulate viscosity, turbidity or both viscosity and turbidity of antisense oligonucleotide solutions wherein the antisense oligonucleotide is present in the solution at a high concentration. In certain embodiments, the present disclosure provides a number of excipients that reduce both the turbidity and the viscosity of an antisense oligonucleotide solution and wherein the excipient also modulates the osmolality of the antisense oligonucleotide solution. In certain embodiments, the present disclosure provides a number of excipients that modulate viscosity, turbidity, or osmolality or viscosity and turbidity and osmolality of an antisense oligonucleotide solution and wherein the antisense oligonucleotide is present in the solution at a high concentration.

The present disclosure provides the following non-limiting numbered embodiments:

Embodiment 1. An aqueous solution comprising:
an antisense oligonucleotide; and
at least one excipient that modulates viscosity, turbidity or both viscosity and turbidity;
wherein the dynamic viscosity of the solution is less than 100 cP at at 25° C.

Embodiment 2. The solution of embodiment 1, having a dynamic viscosity of less than 90 cP at 25° C.

Embodiment 3. The solution of embodiment 1, having a dynamic viscosity of less than 80 cP at 25° C.

Embodiment 4. The solution of embodiment 1, having a dynamic viscosity of less than 70 cP at 25° C.

Embodiment 5. The solution of embodiment 1, having a dynamic viscosity of less than 60 cP at 25° C.

Embodiment 6. The solution of embodiment 1, having a dynamic viscosity of less than 50 cP at 25° C.

Embodiment 7. The solution of embodiment 1, having a dynamic viscosity of less than 40 cP at 25° C.

Embodiment 8. The solution of embodiment 1, having a dynamic viscosity of less than 30 cP at 25° C.

Embodiment 9. The solution of embodiment 1, having a dynamic viscosity of less than 20 cP at 25° C.

Embodiment 10. The solution of embodiment 1, having a dynamic viscosity of less than 10 cP at 25° C.

Embodiment 11. The solution of any of embodiments 1-10, having a turbidity of in the range of 0 to 4000 NTU.

Embodiment 12. The solution of any of embodiments 1-10, having a turbidity of in the range of 0 to 3000 NTU.

Embodiment 13. The solution of any of embodiments 1-10, having a turbidity of in the range of 0 to 2000 NTU.

Embodiment 14. The solution of any of embodiments 1-10, having a turbidity of in the range of 0 to 1000 NTU.

Embodiment 15. The solution of any of embodiments 1-10, having a turbidity of in the range of 0 to 100 NTU.

Embodiment 16. The solution of any of embodiments 1-10, having a turbidity of in the range of 0 to 90 NTU.

Embodiment 17. The solution of any of embodiments 1-10, having a turbidity of the solution is in the range of 0 to 80 NTU.

Embodiment 18. The solution of any of embodiments 1-10, having a turbidity in the range of 0 to 70 NTU.

Embodiment 19. The solution of any of embodiments 1-10, having a turbidity in the range of 0 to 60 NTU.

Embodiment 20. The solution of any of embodiments 1-10, having a turbidity in the range of 0 to 50 NTU.

Embodiment 21. The solution of any of embodiments 1-10, having a turbidity in the range of 0 to 40 NTU.

Embodiment 22. The solution of any of embodiments 1-10, having a turbidity in the range of 0 to 30 NTU.

Embodiment 23. The solution of any of embodiments 1-10, having a turbidity in the range of 0 to 25 NTU.

Embodiment 24. The solution of any of embodiments 1-10, having a turbidity in the range of 0 to 20 NTU.

Embodiment 25. The solution of any of embodiments 1-10, having a turbidity in the range of 0 to 15 NTU.

Embodiment 26. The solution of any of embodiments 1-10, having a turbidity in the range of 0 to 10 NTU.

Embodiment 27. The solution of any of embodiments 1-10, having a turbidity in the range of 0 to 5 NTU.

Embodiment 28. The solution of any of embodiments 1 to 27, wherein the antisense oligonucleotide is present at a concentration of 1 mg/ml to 500 mg/ml.

Embodiment 29. The solution of any of embodiments 1 to 27, wherein the antisense oligonucleotide is present at a concentration of 1 to 400 mg/mL.

Embodiment 30. The solution of any of embodiments 1 to 27, wherein the antisense oligonucleotide is present at a concentration of 1 to 300 mg/mL.

Embodiment 31. The solution of any of embodiments 1 to 27, wherein the antisense oligonucleotide is present at a concentration of 1 to 280 mg/mL.

Embodiment 32. The solution of any of embodiments 1 to 27, wherein the antisense oligonucleotide is present at a concentration of 1 to 260 mg/mL.

Embodiment 33. The solution of any of embodiments 1 to 27, wherein the antisense oligonucleotide is present at a concentration of 1 to 240 mg/mL.

Embodiment 34. The solution of any of embodiments 1 to 27, wherein the antisense oligonucleotide is present at a concentration of 1 to 220 mg/mL.

Embodiment 35. The solution of any of embodiments 1 to 27, wherein the antisense oligonucleotide is present at a concentration of 1 to 200 mg/mL.

Embodiment 36. The solution of any of embodiments 1 to 27, wherein the antisense oligonucleotide is present at a concentration of 100 to 220 mg/mL.

Embodiment 37. The solution of any of embodiments 1 to 27, wherein the antisense oligonucleotide is present at a concentration of 120 to 220 mg/mL.

Embodiment 38. The solution of any of embodiments 1 to 27, wherein the antisense oligonucleotide is present at a concentration of 140 to 220 mg/mL.

Embodiment 39. The solution of any of embodiments 1 to 27, wherein the antisense oligonucleotide is present at a concentration of 160 to 220 mg/mL.

Embodiment 40. The solution of any of embodiments 1 to 27, wherein the antisense oligonucleotide is present at a concentration of 180 to 220 mg/mL.

Embodiment 41. The solution of any of embodiments 1 to 27, wherein the antisense oligonucleotide is present at a concentration of 130 to 170 mg/mL.

Embodiment 42. The solution of any of embodiments 1 to 27, wherein the antisense oligonucleotide is present at a concentration of 135 to 165 mg/mL.

Embodiment 43. The solution of any of embodiments 1 to 27, wherein the antisense oligonucleotide is present at a concentration of 140 to 160 mg/mL.

Embodiment 44. The solution of any of embodiments 1 to 27, wherein the antisense oligonucleotide is present at a concentration of 145 to 155 mg/mL.

Embodiment 45. The solution of any of embodiments 1 to 27, wherein the antisense oligonucleotide is present at a concentration of 150 mg/mL.

Embodiment 46. The solution of any of embodiments 1 to 27, wherein the antisense oligonucleotide is present at a concentration of 50 mg/mL.

Embodiment 47. The solution of any of embodiments 1 to 27, wherein the antisense oligonucleotide is present at a concentration of 40 mg/mL.

Embodiment 48. The solution of any of embodiments 1 to 27, wherein the antisense oligonucleotide is present at a concentration of 60 mg/mL.

Embodiment 49. The solution of any of embodiments 1 to 48, wherein at least one of the at least one excipient that modulates viscosity, turbidity or both viscosity and turbidity comprises an aromatic compound.

Embodiment 50. The solution of any of embodiments 1 to 48, wherein at least one of the at least one excipient that modulates viscosity, turbidity or both viscosity and turbidity is an aromatic compound.

Embodiment 51. The solution of any of embodiments 1 to 50, wherein at least one of the at least one excipient that modulates viscosity, turbidity or both viscosity and turbidity is a heterocyclic compound.

Embodiment 52. The solution of any of embodiments 1 to 51, wherein at least one of the at least one excipient that modulates viscosity, turbidity or both viscosity and turbidity is a heterocyclic aromatic compound.

Embodiment 53. The solution of any of embodiments 1 to 50, wherein at least one of the at least one excipient that modulates viscosity, turbidity or both viscosity and turbidity comprises a heterocyclic compound.

Embodiment 54. The solution of embodiment 51 or 52, wherein the heteroatom of the heterocyclic compound is nitrogen.

Embodiment 55. The solution of embodiment 51 or 52, wherein the heteroatom of the heterocyclic compound is oxygen.

Embodiment 56. The solution of embodiment 51 or 52, wherein the heteroatom of the heterocyclic compound is not oxygen.

Embodiment 57. The solution of embodiment 51 or 52, wherein the heteroatom of the heterocyclic compound is sulfur.

Embodiment 58. The solution of any of embodiments 51 to 57, wherein heterocyclic compound has more than one heteroatom.

Embodiment 59. The solution of any of embodiments 51 to 57, wherein heterocyclic compound has two or more heteroatoms.

Embodiment 60. The solution of any of embodiments 51 to 59, wherein heterocyclic compound comprises a monocyclic ring having two or more heteroatoms.

Embodiment 61. The solution of any of embodiments 51 to 59, wherein heterocyclic compound is a heterocyclic aromatic compound that comprises a monocyclic ring having two or more heteroatoms.

Embodiment 62. The solution of any of embodiments 60 to 61 where the heteroatoms are different.

Embodiment 63. The solution of any of embodiments 60 to 61 where the heteroatoms are the same.

Embodiment 64. The solution of embodiment 60 or 63, wherein the heteroatom of the heterocyclic compound is nitrogen.

Embodiment 65. The solution of embodiment 60 or 63, wherein the heteroatom of the heterocyclic compound is oxygen.

Embodiment 66. The solution of embodiment 60 or 63, wherein the heteroatom of the heterocyclic compound is not oxygen.

Embodiment 67. The solution of embodiment 60 or 63, wherein the heteroatom of the heterocyclic compound is sulfur.

Embodiment 68. The solution of any of embodiments 1 to 52, wherein at least one of the at least one excipient that modulates viscosity, turbidity or both viscosity and turbidity is a pyridine.

Embodiment 69. The solution of any of embodiments 1 to 52, wherein at least one of the at least one excipient that modulates viscosity, turbidity or both viscosity and turbidity is a diazine.

Embodiment 70. The solution of embodiment 69, wherein the diazine is 1,2-diazine.

Embodiment 71. The solution of embodiment 69, wherein the diazine is 1,3-diazine.

Embodiment 72. The solution of embodiment 69, wherein the diazine is 1,4-diazine.

Embodiment 73. The solution of any of embodiments 1 to 52, wherein at least one of the at least one excipient that modulates viscosity, turbidity or both viscosity and turbidity is an imidazole.

Embodiment 74. The solution of any of embodiments 1 to 52, wherein at least one of the at least one excipient that modulates viscosity, turbidity or both viscosity and turbidity is a tetrazine.

Embodiment 75. The solution of any of embodiments 1 to 52, wherein at least one of the at least one excipient that modulates viscosity, turbidity or both viscosity and turbidity is a hexazine.

Embodiment 76. The solution of embodiment 53, wherein the heterocyclic compound comprises a heterocyclic amine.

Embodiment 77. The solution of any of embodiments 1 to 69, wherein the excipient is a hydrogen bond doner.

Embodiment 78. The solution of any of embodiments 1 to 69, wherein the excipient is a hydrogen bond acceptor.

Embodiment 79. The solution of any of embodiments 1 to 78, wherein at least one of the at least one excipient that modulates viscosity, turbidity or both viscosity and turbidityis selected from the group consisting of Adenine, Benzyl Alcohol, m-Cresol, Cytidine, Cytidine Monophosphate, Cytosine, Dextran, Guanine Monophosphate, D-Mannitol, Methylparaben, Nicotinamide, Phenol, 2-Phenoxyethanol, L-Phenylalanine, Pyridoxine, Sodium Chloride, Thymine, tryptophan, L-Tryptophan, L-Tyrosine, Ascorbic Acid, Benzamide, o-Benzenediol, Benzenehexol, L-Histidine, Hydroxypyridine, Indole, D-Mannitol+Phenol mixture, D-Mannitol+Pyridine mixture, 2H-Pyran, Pyrazinamide, Pyridine, Pyrimidine, 2-Pyrone, Riboflavin, Thiamine, Tryptamine, ethanol, (2-Hydroxypropyl)-β-cyclodextrin, Niacin, Polyethylene Glycol 600, Polyethylene Glycol 4600, Propylene Glycol, Pyridoxine, Sucrose, Thymidine, Tween 80, Uridine, Thymine, caffeine, acridine orange, ethidium bromide, propidium iodide, cyanine dyes such as PicoGreen®, thiamine hydrochloride, ethylene diamine tetraacetic acid, 1,2-dihydroxybenzene, 1,2-dihydroxybenzene (catechol), D-Mannitol+phenol mixture, D-Mannitol+niacinamide mixture, calcium folinate, L-phenylalanine+pyridoxine mixture, pyridoxine+benzyl alcohol mixture, pyridoxine HCl+benzyl alcohol mixture, niacin sodium salt, dextran 1500, and pyridoxine HCl+phenylalanine mixture.

Embodiment 80. The solution of embodiment 79, wherein at least one of the at least one excipient that modulates viscosity, turbidity or both viscosity and turbidity is Adenine.

Embodiment 81. The solution of embodiment 79, wherein at least one of the at least one excipient that modulates viscosity, turbidity or both viscosity and turbidity is Benzyl Alcohol.

Embodiment 82. The solution of embodiment 79, wherein at least one of the one or more excipient is m-Cresol.

Embodiment 83. The solution of embodiment 79, wherein at least one of the at least one excipient that modulates viscosity, turbidity or both viscosity and turbidity is Cytidine.

Embodiment 84. The solution of embodiment 79, wherein at least one of the at least one excipient that modulates viscosity, turbidity or both viscosity and turbidity is Cytidine Monophosphate.

Embodiment 85. The solution of embodiment 79, wherein at least one of the at least one excipient that modulates viscosity, turbidity or both viscosity and turbidity is Cytosine.

Embodiment 86. The solution of embodiment 79, wherein at least one of the at least one excipient that modulates viscosity, turbidity or both viscosity and turbidity is Dextran.

Embodiment 87. The solution of embodiment 79, wherein at least one of the at least one excipient that modulates viscosity, turbidity or both viscosity and turbidity is Guanine Monophosphate.

Embodiment 88. The solution of embodiment 79, wherein at least one of the at least one excipient that modulates viscosity, turbidity or both viscosity and turbidity is D-Mannitol.

Embodiment 89. The solution of embodiment 79, wherein at least one of the at least one excipient that modulates viscosity, turbidity or both viscosity and turbidity is Methylparaben.

Embodiment 90. The solution of embodiment 79, wherein at least one of the at least one excipient that modulates viscosity, turbidity or both viscosity and turbidity is Nicotinamide.

Embodiment 91. The solution of embodiment 79, wherein at least one of the at least one excipient that modulates viscosity, turbidity or both viscosity and turbidity is Phenol.

Embodiment 92. The solution of embodiment 79, wherein at least one of the at least one excipient that modulates viscosity, turbidity or both viscosity and turbidity is 2-Phenoxyethanol.

Embodiment 93. The solution of embodiment 79, wherein at least one of the at least one excipient that modulates viscosity, turbidity or both viscosity and turbidity is L-Phenylalanine.

Embodiment 94. The solution of embodiment 79, wherein at least one of the at least one excipient that modulates viscosity, turbidity or both viscosity and turbidity is Pyridoxine.

Embodiment 95. The solution of embodiment 79, wherein at least one of at least one excipient that modulates viscosity, turbidity or both viscosity and turbidity is Sodium Chloride.

Embodiment 96. The solution of embodiment 79, wherein at least one of at least one excipient that modulates viscosity, turbidity or both viscosity and turbidity is Thymine.

Embodiment 97. The solution of embodiment 79, wherein at least one of the at least one excipient that modulates viscosity, turbidity or both viscosity and turbidity is L-Tryptophan.

Embodiment 98. The solution of embodiment 79, wherein at least one of the at least one excipient that modulates viscosity, turbidity or both viscosity and turbidity is tryptophan.

Embodiment 99. The solution of embodiment 79, wherein at least one of the at least one excipient that modulates viscosity, turbidity or both viscosity and turbidity is L-Tyrosine.

Embodiment 100. The solution of embodiment 79, wherein at least one of the at least one excipient that modulates viscosity, turbidity or both viscosity and turbidity is Ascorbic Acid.

Embodiment 101. The solution of embodiment 79, wherein at least one of the at least one excipient that modulates viscosity, turbidity or both viscosity and turbidity is Benzamide.

Embodiment 102. The solution of embodiment 79, wherein at least one of the one or more excipient is o-Benzenediol.

Embodiment 103. The solution of embodiment 79, wherein at least one of the at least one excipient that modulates viscosity, turbidity or both viscosity and turbidity is Benzenehexol.

Embodiment 104. The solution of embodiment 79, wherein at least one of the one or more excipient is L-Histidine.

Embodiment 105. The solution of embodiment 79, wherein at least one of the at least one excipient that modulates viscosity, turbidity or both viscosity and turbidity is a hydroxypyridine.

Embodiment 106. The solution of embodiment 79, wherein at least one of the at least one excipient that modulates viscosity, turbidity or both viscosity and turbidity is an indole.

Embodiment 107. The solution of embodiment 79, wherein at least one of the at least one excipient that modulates viscosity, turbidity or both viscosity and turbidity is D-Mannitol.

Embodiment 108. The solution of embodiment 79, wherein at least one of the at least one excipient that modulates viscosity, turbidity or both viscosity and turbidity is a D-Mannitol and phenol mixture.

Embodiment 109. The solution of embodiment 79, wherein at least one of at least one excipient that modulates viscosity, turbidity or both viscosity and turbidity is a D-Mannitol and pyridine mixture.

Embodiment 110. The solution of embodiment 79, wherein at least one of at least one excipient that modulates viscosity, turbidity or both viscosity and turbidity is 2H-Pyran.

Embodiment 111. The solution of embodiment 79, wherein at least one of at least one excipient that modulates viscosity, turbidity or both viscosity and turbidity is a pyrazinamide.

Embodiment 112. The solution of embodiment 79, wherein at least one of at least one excipient that modulates viscosity, turbidity or both viscosity and turbidity is a pyridine.

Embodiment 113. The solution of embodiment 79, wherein at least one of at least one excipient that modulates viscosity, turbidity or both viscosity and turbidity is a pyrimidine.

Embodiment 114. The solution of embodiment 79, wherein at least one of the at least one excipient that modulates viscosity, turbidity or both viscosity and turbidity is 2-Pyrone.

Embodiment 115. The solution of embodiment 79, wherein at least one of the at least one excipient that modulates viscosity, turbidity or both viscosity and turbidity is riboflavin.

Embodiment 116. The solution of embodiment 79, wherein at least one of the at least one excipient that modulates viscosity, turbidity or both viscosity and turbidity is thiamine.

Embodiment 117. The solution of embodiment 79, wherein at least one of the at least one excipient that modulates viscosity, turbidity or both viscosity and turbidity is tryptamine.

Embodiment 118. The solution of embodiment 79, wherein at least one of the at least one excipient that modulates viscosity, turbidity or both viscosity and turbidity is ethanol.

Embodiment 119. The solution of embodiment 79, wherein at least one of the at least one excipient that modulates viscosity, turbidity or both viscosity and turbidity is (2-Hydroxypropyl)-β-cyclodextrin.

Embodiment 120. The solution of embodiment 79, wherein at least one of the at least one excipient that modulates viscosity, turbidity or both viscosity and turbidity is Niacin.

Embodiment 121. The solution of embodiment 79, wherein at least one of the at least one excipient that modulates viscosity, turbidity or both viscosity and turbidity is Polyethylene Glycol 790.

Embodiment 122. The solution of embodiment 79, wherein at least one of the at least one excipient that modulates viscosity, turbidity or both viscosity and turbidity is Polyethylene Glycol 4790.

Embodiment 123. The solution of embodiment 79, wherein at least one of the at least one excipient that modulates viscosity, turbidity or both viscosity and turbidity is Propylene Glycol.

Embodiment 124. The solution of embodiment 79, wherein at least one of the at least one excipient that modulates viscosity, turbidity or both viscosity and turbidity is Pyridoxine.

Embodiment 125. The solution of embodiment 79, wherein at least one of the at least one excipient that modulates viscosity, turbidity or both viscosity and turbidity is Sucrose.

Embodiment 126. The solution of embodiment 79, wherein at least one of the at least one excipient that modulates viscosity, turbidity or both viscosity and turbidity is Thymidine.

Embodiment 127. The solution of embodiment 79, wherein at least one of the at least one excipient that modulates viscosity, turbidity or both viscosity and turbidity is Tween 80.

Embodiment 128. The solution of embodiment 79, wherein at least one of the at least one excipient that modulates viscosity, turbidity or both viscosity and turbidity is Uridine.

Embodiment 129. The solution of embodiment 79, wherein at least one of the at least one excipient that modulates viscosity, turbidity or both viscosity and turbidity is Thymine.

Embodiment 130. The solution of embodiment 79, wherein at least one of the at least one excipient that modulates viscosity, turbidity or both viscosity and turbidity is caffeine.

Embodiment 131. The solution of embodiment 79, wherein at least one of the at least one excipient that modulates viscosity, turbidity or both viscosity and turbidity is acridine orange.

Embodiment 132. The solution of embodiment 79, wherein at least one of the at least one excipient that modulates viscosity, turbidity or both viscosity and turbidity is ethidium bromide.

Embodiment 133. The solution of embodiment 79, wherein at least one of the at least one excipient that modulates viscosity, turbidity or both viscosity and turbidity is propidium iodide.

Embodiment 134. The solution of embodiment 79, wherein at least one of the at least one excipient that modulates viscosity, turbidity or both viscosity and turbidity is a cyanine dye.

Embodiment 135. The solution of embodiment 79, wherein at least one of the at least one excipient that modulates viscosity, turbidity or both viscosity and turbidity is PicoGreen®.

Embodiment 136. The solution of embodiment 79, wherein at least one of the at least one excipient that modulates viscosity, turbidity or both viscosity and turbidity is 1,2-dihydroxybenzene (catechol).

Embodiment 137. The solution of embodiment 79, wherein at least one of the at least one excipient that modulates viscosity, turbidity or both viscosity and turbidity is D-Mannitol+phenol mixture.

Embodiment 138. The solution of embodiment 79, wherein at least one of the at least one excipient that modulates viscosity, turbidity or both viscosity and turbidity is D-Mannitol+niacinamide mixture.

Embodiment 139. The solution of embodiment 79, wherein at least one of the at least one excipient that modulates viscosity, turbidity or both viscosity and turbidity is calcium folinate.

Embodiment 140. The solution of embodiment 79, wherein at least one of the at least one excipient that modulates viscosity, turbidity or both viscosity and turbidity is L-phenylalanine+pyridoxine mixture.

Embodiment 141. The solution of embodiment 79, wherein at least one of the at least one excipient that modulates viscosity, turbidity or both viscosity and turbidity is pyridoxine+benzyl alcohol mixture.

Embodiment 142. The solution of embodiment 79, wherein at least one of the at least one excipient that modulates viscosity, turbidity or both viscosity and turbidity is pyridoxine HCl+benzyl alcohol mixture.

Embodiment 143. The solution of embodiment 79, wherein at least one of the at least one excipient that modulates viscosity, turbidity or both viscosity and turbidity is pyridoxine HCl+phenylalanine mixture.

Embodiment 144. The solution of embodiment 79, wherein at least one of the at least one excipient that modulates viscosity, turbidity or both viscosity and turbidity is D-Mannitol (0.5% w/v)+phenol (0.5% w/v) mixture.

Embodiment 145. The solution of embodiment 79, wherein at least one of the at least one excipient that modulates viscosity, turbidity or both viscosity and turbidity is D-Mannitol (0.5% w/v)+niacinamide (0.5% w/v) mixture.

Embodiment 146. The solution of embodiment 79, wherein at least one of the at least one excipient that modulates viscosity, turbidity or both viscosity and turbidity is D-Mannitol (0.5% w/v)+pyridine (0.5% w/v) mixture.

Embodiment 147. The solution of embodiment 79, wherein at least one of the at least one excipient that modulates viscosity, turbidity or both viscosity and turbidity is L-phenylalanine (1.0% w/v)+pyroxidine (0.5% w/v) mixture.

Embodiment 148. The solution of embodiment 79, wherein at least one of the at least one excipient that modulates viscosity, turbidity or both viscosity and turbidity is pyroxidine (0.5% w/v)+benzyl alcohol (0.5% w/v) mixture.

Embodiment 149. The solution of embodiment 79, wherein at least one of the at least one excipient that modulates viscosity, turbidity or both viscosity and turbidity is pyroxidine HCl (0.5% w/v)+benzyl alcohol (0.5% w/v) mixture.

Embodiment 150. The solution of embodiment 79, wherein at least one of the at least one excipient that modulates viscosity, turbidity or both viscosity and turbidity is pyroxidine HCl (0.5% w/v)+phenylalanine (1.0% w/v) mixture.

Embodiment 151. The solution of any of embodiments 1 to 150, wherein the solution does not comprise cyclodextrin.

Embodiment 152. The solution of any of embodiments 1 to 150, wherein the solution does not comprise mannitol.

Embodiment 153. The solution of any of embodiments 1 to 152, wherein at least one of the at least one excipient that modulates viscosity, turbidity or both viscosity and turbidity is an antimicrobial.

Embodiment 154. The solution of any of embodiments 1 to 153, wherein at least one of the at least one excipient that modulates viscosity, turbidity or both viscosity and turbidity is not an antimicrobial.

Embodiment 155. The solution of any of embodiments 1 to 152 or 154, wherein the solution does not comprise any excipient that is an antimicrobial.

Embodiment 156. The solution of any of embodiments 1 to 155, wherein at least one of the at least one excipient that modulates viscosity, turbidity or both viscosity and turbidity increases the osmolarity of the solution.

Embodiment 157. The solution of any of embodiments 1 to 156, wherein at least one of the at least one excipient that modulates viscosity, turbidity or both viscosity and turbidity increases the pH of the solution.

Embodiment 158. The solution of any of embodiments 1 to 156, wherein at least one of the at least one excipient that modulates viscosity, turbidity or both viscosity and turbidity decreases the pH of the solution.

Embodiment 159. The solution of any of embodiments 1 to 158, wherein at least one of the at least one excipient that modulates viscosity, turbidity or both viscosity and turbidity buffers the pH of the solution.

Embodiment 160. The solution of any of embodiments 1 to 159, wherein the solution comprises only one excipient that modulates viscosity, turbidity or both viscosity and turbidity.

Embodiment 161. The solution of any of embodiments 1 to 160, wherein the solution comprises only one excipient.

Embodiment 162. The solution of any of embodiments 1 to 160, wherein the solution comprises at least two excipients.

Embodiment 163. The solution of any of embodiments 1 to 160, wherein the solution comprises at least three excipients.

Embodiment 164. The solution of any of embodiments 1 to 160, wherein the solution comprises at least four excipients.

Embodiment 165. The solution of any of embodiments 1 to 160, wherein the solution comprises at least two excipients that modulate viscosity, turbidity or both.

Embodiment 166. The solution of any of embodiments 1 to 160, wherein the solution comprises at least three excipients that modulate viscosity, turbidity or both.

Embodiment 167. The solution of any of embodiments 1 to 160, wherein the solution comprises at least four excipients that modulate viscosity, turbidity or both.

Embodiment 168. The solution of any of embodiments 1 to 167, wherein the total amount of excipient in the solution is in the range of 0.1 to 7 parts by weight.

Embodiment 169. The solution of any of embodiments 1 to 167, wherein the total amount of excipient in the solution is in the range of 0.3 to 7 parts by weight.

Embodiment 170. The solution of any of embodiments 1 to 167, wherein the total amount of excipient in the solution is in the range of 0.5 to 5 parts by weight.

Embodiment 171. The solution of any of embodiments 1 to 167, wherein the total amount of excipient in the solution is in the range of 1 to 5 parts by weight.

Embodiment 172. The solution of any of embodiments 1 to 167, wherein the total amount of excipient in the solution is in the range of 2 to 5 parts by weight.

Embodiment 173. The solution of any of embodiments 1 to 167, wherein the total amount of excipient in the solution is in the range of 3 to 5 parts by weight.

Embodiment 174. The solution of any of embodiments 1 to 167, wherein the total amount of excipient in the solution is in the range of 4 to 5 parts by weight.

Embodiment 175. The solution of any of embodiments 1 to 167, wherein the total amount of excipient in the solution is in the range of 4.5 to 5.5 parts by weight.

Embodiment 176. The solution of any of embodiments 1 to 167, wherein the total amount of excipient that modulates viscosity, turbidity or both in the solution is in the range of 0.1 to 7 parts by weight.

Embodiment 177. The solution of any of embodiments 1 to 167, wherein the total amount of excipient that modulates viscosity, turbidity or both in the solution is in the range of 0.3 to 7 parts by weight.

Embodiment 178. The solution of any of embodiments 1 to 167, wherein the total amount of excipient that modulates viscosity, turbidity or both in the solution is in the range of 0.5 to 5 parts by weight.

Embodiment 179. The solution of any of embodiments 1 to 167, wherein the total amount of excipient that modulates viscosity, turbidity or both in the solution is in the range of 1 to 5 parts by weight.

Embodiment 180. The solution of any of embodiments 1 to 167, wherein the total amount of excipient that modulates viscosity, turbidity or both in the solution is in the range of 2 to 5 parts by weight.

Embodiment 181. The solution of any of embodiments 1 to 167, wherein the total amount of excipient that modulates viscosity, turbidity or both in the solution is in the range of 3 to 5 parts by weight.

Embodiment 182. The solution of any of embodiments 1 to 167, wherein the total amount of excipient that modulates viscosity, turbidity or both in the solution is in the range of 4 to 5 parts by weight.

Embodiment 183. The solution of any of embodiments 1 to 167, wherein the total amount of excipient that modulates viscosity, turbidity or both in the solution is in the range of 4.5 to 5.5 parts by weight.

Embodiment 184. The solution of any of embodiments 1 to 183, wherein the antisense oligonucleotide comprises at least one modified nucleoside.

Embodiment 185. The solution of embodiment 184, wherein at least one modified nucleoside comprises a modified sugar moiety.

Embodiment 186. The solution of embodiment 185, wherein at least one modified sugar moiety is a 2'-substituted sugar moiety.

Embodiment 187. The solution of embodiment 186, wherein the 2'-substitutent of at least one 2'-substituted sugar moiety is selected from among: 2'-OMe, 2'-F, and 2'-MOE.

Embodiment 188. The solution of embodiment 187, wherein the 2'-substituent of at least one 2'-substituted sugar moiety is a 2'-MOE.

Embodiment 189. The solution of any of embodiments 1 to 188, wherein at least one modified sugar moiety is a bicyclic sugar moiety.

Embodiment 190. The solution of embodiment 189, wherein at least one bicyclic sugar moiety is LNA or cEt.

Embodiment 191. The solution of any of embodiments 1 to 191, wherein at least one sugar moiety is a sugar surrogate.

Embodiment 192. The solution of embodiment 191, wherein at least one sugar surrogate is a morpholino.

Embodiment 193. The solution of embodiment 191, wherein at least one sugar surrogate is a modified morpholino.

Embodiment 194. The solution of any of embodiments 1 to 193, wherein the antisense oligonucleotide comprises at least 5 modified nucleosides, each independently comprising a modified sugar moiety.

Embodiment 195. The solution of any of embodiments 1 to 193, wherein the antisense oligonucleotide comprises at least 10 modified nucleosides, each independently comprising a modified sugar moiety.

Embodiment 196. The solution of any of embodiments 1 to 193, wherein the antisense oligonucleotide comprises at least 15 modified nucleosides, each independently comprising a modified sugar moiety.

Embodiment 197. The solution of any of embodiments 1 to 196, wherein each nucleoside of the antisense oligonucleotide is a modified nucleoside, each independently comprising a modified sugar moiety Embodiment 198. The solution of any of any of embodiments 1 to 197, wherein the antisense oligonucleotide comprises at least two modified nucleosides comprising modified sugar moieties that are the same as one another.

Embodiment 199. The solution of any of embodiments 1 to 198, wherein the antisense oligonucleotide comprises at least two modified nucleosides comprising modified sugar moieties that are different from one another.

Embodiment 200. The solution of any of embodiments 1 to 199, wherein the antisense oligonucleotide comprises a modified region of at least 5 contiguous modified nucleosides.

Embodiment 201. The solution of any of embodiments 1 to 200, wherein the antisense oligonucleotide comprises a modified region of at least 10 contiguous modified nucleosides.

Embodiment 202. The solution of any of embodiments 1 to 201, wherein the antisense oligonucleotide comprises a modified region of at least 15 contiguous modified nucleosides.

Embodiment 203. The solution of any of embodiments 1 to 202, wherein the antisense oligonucleotide comprises a modified region of at least 20 contiguous modified nucleosides.

Embodiment 204. The solution of any of embodiments 197 to 203, wherein each modified nucleoside of the modified region has a modified sugar moiety independently selected from among: 2'-F, 2'-OMe, 2'-MOE, cEt, LNA, morpholino, and modified morpholino.

Embodiment 205. The solution of any of embodiments 197 to 203, wherein the modified nucleosides of the modified region each comprise the same modification as one another.

Embodiment 206. The solution of embodiment 205, wherein the modified nucleosides of the modified region each comprise the same 2'-substituted sugar moiety.

Embodiment 207. The solution of embodiment 206, wherein the 2'-substituted sugar moiety of the modified nucleosides of the region of modified nucleosides is selected from 2'-F, 2'-OMe, and 2'-MOE.

Embodiment 208. The solution of embodiment 207, wherein the 2'-substituted sugar moiety of the modified nucleosides of the region of modified nucleosides is 2'-MOE.

Embodiment 209. The solution of embodiment 205, wherein the modified nucleosides of the region of modified nucleosides each comprise the same bicyclic sugar moiety.

Embodiment 210. The solution of embodiment 209, wherein the bicyclic sugar moiety of the modified nucleosides of the region of modified nucleosides is selected from LNA and cEt.

Embodiment 211. The solution of embodiment 205, wherein the modified nucleosides of the region of modified nucleosides each comprises a sugar surrogate.

Embodiment 212. The solution of embodiment 211, wherein the sugar surrogate of the modified nucleosides of the region of modified nucleosides is a morpholino.

Embodiment 213. The solution of embodiment 211, wherein the sugar surrogate of the modified nucleosides of the region of modified nucleosides is a modified morpholino.

Embodiment 214. The solution of any of embodiments 1 to 213, wherein the modified nucleotide comprises no more than 4 contiguous naturally occurring nucleosides.

Embodiment 215. The solution of any of embodiments 1 to 214, wherein each nucleoside of the antisense oligonucleotide is a modified nucleoside.

Embodiment 216. The solution of embodiment 215 wherein each modified nucleoside comprises a modified sugar moiety.

Embodiment 217. The solution of embodiment 216, wherein the modified nucleosides of the antisense oligonucleotide comprise the same modification as one another.

Embodiment 218. The solution of embodiment 217, wherein the modified nucleosides of the antisense oligonucleotide each comprise the same 2'-substituted sugar moiety.

Embodiment 219. The solution of embodiment 218, wherein the 2'-substituted sugar moiety of the antisense oligonucleotide is selected from 2'-F, 2'-OMe, and 2'-MOE.

Embodiment 220. The solution of embodiment 219, wherein the 2'-substituted sugar moiety of the antisense oligonucleotide is 2'-MOE.

Embodiment 221. The solution of embodiment 217, wherein the modified nucleosides of the antisense oligonucleotide each comprise the same bicyclic sugar moiety.

Embodiment 222. The solution of embodiment 221, wherein the bicyclic sugar moiety of the antisense oligonucleotide is selected from LNA and cEt.

Embodiment 223. The solution of embodiment 217, wherein the modified nucleosides of the antisense oligonucleotide each comprises a sugar surrogate.

Embodiment 224. The solution of embodiment 223, wherein the sugar surrogate of the antisense oligonucleotide is a morpholino.

Embodiment 225. The solution of embodiment 223, wherein the sugar surrogate of the antisense oligonucleotide is a modified morpholino.

Embodiment 226. The solution of any of embodiments 1 to 225, wherein the antisense oligonucleotide comprises at least one modified internucleoside linkage.

Embodiment 227. The solution of embodiment 226, wherein each internucleoside linkage is a modified internucleoside linkage.

Embodiment 228. The solution of embodiment 226 or 227, comprising at least one phosphorothioate internucleoside linkage.

Embodiment 229. The solution of embodiment 227, wherein each internucleoside linkage is a modified internucleoside linkage and wherein each internucleoside linkage comprises the same modification.

Embodiment 230. The solution of embodiment 229, wherein each internucleoside linkage is a phosphorothioate internucleoside linkage.

Embodiment 231. The solution of any of embodiments 1 to 230, comprising at least one conjugate.

Embodiment 232. The solution of any of embodiments 1 to 231, wherein the antisense oligonucleotide consists of a single-strand antisense oligonucleotide.

Embodiment 233. The solution of any of embodiments 1 to 232, wherein the antisense oligonucleotide consists of a double-strand antisense oligonucleotide.

Embodiment 234. The solution of any of embodiments 1 to 233, wherein the antisense oligonucleotide is selected from the group consisting of ISIS 426115, ISIS 104838, ISIS 416858, ISIS 420915, ISIS 494372, ISIS 487660, ISIS 404173, ISIS 449884, ISIS 501861, ISIS 540175, ISIS 396443, ISIS 463588, ISIS 301012, ISIS 329993, ISIS 304801, ISIS 426115, ISIS 481464, ISIS 183750, and ISIS 333611.

Embodiment 235. The solution of any of embodiments 1 to 234, wherein the antisense oligonucleotide has a dynamic viscosity of more than 60 cP at 25° C. when mixed in water or saline solution in the absence of an excipient that modulates viscosity, turbidity or both viscosity and turbidity.

Embodiment 236. The solution of any of embodiments 1 to 234, wherein the antisense oligonucleotide has a dynamic viscosity of more than 55 cP at 25° C. when mixed in water or saline solution and in the absence of an excipient that modulates viscosity, turbidity or both viscosity and turbidity.

Embodiment 237. The solution of any of embodiments 1 to 234, wherein the antisense oligonucleotide has a dynamic viscosity of more than 50 cP at 25° C. when mixed in water or saline solution and in the absence of an excipient that modulates viscosity, turbidity or both viscosity and turbidity.

Embodiment 238. The solution of any of embodiments 1 to 234, wherein the antisense oligonucleotide has a dynamic viscosity of more than 45 cP at 25° C. when mixed in water or saline solution and in the absence of an excipient that modulates viscosity, turbidity or both viscosity and turbidity.

Embodiment 239. The solution of any of embodiments 1 to 234, wherein the antisense oligonucleotide has a dynamic viscosity of more than 40 cP at 25° C. when mixed in water or saline solution and in the absence of an excipient that modulates viscosity, turbidity or both viscosity and turbidity.

Embodiment 240. The solution of any of embodiments 1 to 234, wherein the antisense oligonucleotide has a turbidity of more than 100 NTU when mixed in water or saline solution and in the absence of an excipient that modulates viscosity, turbidity or both viscosity and turbidity.

Embodiment 241. The solution of any of embodiments 1 to 234, wherein the antisense oligonucleotide has a turbidity of more than 70 NTU when mixed in water or saline solution and in the absence of an excipient that modulates viscosity, turbidity or both viscosity and turbidity.

Embodiment 242. The solution of any of embodiments 1 to 234, wherein the antisense oligonucleotide has a turbidity of more than 50 NTU when mixed in water or saline solution and in the absence of an excipient that modulates viscosity, turbidity or both viscosity and turbidity.

Embodiment 243. The solution of any of embodiments 1 to 234, wherein the antisense oligonucleotide has a turbidity of more than 25 NTU when mixed in water or saline solution and in the absence of an excipient that modulates viscosity, turbidity or both viscosity and turbidity.

Embodiment 244. The solution of any of embodiments 1 to 234, wherein the antisense oligonucleotide has a turbidity of more than 20 NTU when mixed in water or saline solution and in the absence of an excipient that modulates viscosity, turbidity or both viscosity and turbidity.

Embodiment 245. A method of reducing the turbidity of an antisense oligonucleotide solution, said method comprising adding an effective amount of an excipient that modulates viscosity, turbidity or both viscosity and turbidity to the antisense oligonucleotide solution.

Embodiment 246. The method of embodiment 245, wherein the excipient that modulates viscosity, turbidity or both viscosity and turbidity is an excipient according to any of embodiments 49-133.

Embodiment 247. The method of embodiment 245 or 246, wherein the antisense compound is an antisense compound according to any of embodiments 184-234.

Embodiment 248. The method of any of embodiments 245-247, wherein the turbidity is reduced by 0-1000 NTU.

Embodiment 249. The method of any of embodiments 245-247, wherein the turbidity is reduced by 0-500 NTU.

Embodiment 250. The method of any of embodiments 245-247, wherein the turbidity is reduced by 0-100 NTU.

Embodiment 251. The method of any of embodiments 245-247, wherein the turbidity is reduced by 0-50 NTU.

Embodiment 252. The method of any of embodiments 245-247, wherein the turbidity is reduced by 0-30 NTU.

Embodiment 253. The method of any of embodiments 245-247, wherein the turbidity is reduced by 0-20 NTU.

Embodiment 254. The method of any of embodiments 245-247, wherein the turbidity is reduced by 0-10 NTU.

Embodiment 255. A method of reducing the viscosity of an antisense oligonucleotide solution, said method comprising adding an effective amount of an excipient that modulates viscosity, turbidity or both viscosity and turbidity to the antisense oligonucleotide solution.

Embodiment 256. The method of embodiment 255, wherein the excipient that modulates viscosity, turbidity or both viscosity and turbidity is an excipient according to any of embodiments 49-155.

Embodiment 257. The method of embodiment 255 or 256, wherein the antisense compound is an antisense compound according to any of embodiments 184-234.

Embodiment 258. The method of any of embodiments 255-257, wherein the viscosity is reduced by 1-100 cP at 25° C.

Embodiment 259. The method of any of embodiments 255-257, wherein the viscosity is reduced by 1-50 cP at 25° C.

Embodiment 260. The method of any of embodiments 255-257, wherein the viscosity is reduced by 1-40 cP at 25° C.

Embodiment 261. The method of any of embodiments 255-257, wherein the viscosity is reduced by 1-30 cP at 25° C.

Embodiment 262. The method of any of embodiments 255-257, wherein the viscosity is reduced by 1-20 cP at 25° C.

Embodiment 263. The method of any of embodiments 255-257, wherein the viscosity is reduced by 1-10 cP at 25° C.

Embodiment 264. The method of any of embodiments 255-257, wherein the viscosity is reduced by 1-5 cP at 25° C.

Embodiment 265. A method of reducing both the viscosity and the turbidity of an antisense oligonucleotide solution, said method comprising adding an effective amount of an excipient that modulates viscosity, turbidity or both to the antisense oligonucleotide solution.

Embodiment 266. The method of embodiment 265, wherein the excipient that modulates viscosity, turbidity or both viscosity and turbidity is an excipient according to any of embodiments 49-155.

Embodiment 267. The method of embodiment 245 or 246, wherein the antisense compound is an antisense compound according to any of embodiments 184-234.

Embodiment 268. A method of selecting a pharmaceutically acceptable antisense oligonucleotide from among many antisense oligonucleotides, said method comprising:
measuring the dynamic viscosity of an antisense oligonucleotide solution, wherein the solution comprises between 100 mg/mL and 250 mg/mL of the antisense oligonucleotide;
measuring the turbidity of the antisense oligonucleotide solution; and
selecting an antisense oligonucleotide that has a dynamic viscosity below 40 cP and a turbidity below 30 NTU.

Embodiment 269. A method of reducing the turbidity of an antisense oligonucleotide solution, said method comprising adding an effective amount of an excipient that modulates viscosity, turbidity or both viscosity and turbidity to the antisense oligonucleotide solution.

Embodiment 270. The method of embodiment 269, wherein the excipient that modulates viscosity, turbidity or both viscosity and turbidity is an excipient according to any preceeding embodiment.

Embodiment 271. A method of reducing the viscosity of an antisense oligonucleotide solution, said method comprising adding an effective amount of an excipient that modulates viscosity, turbidity or both viscosity and turbidity to the antisense oligonucleotide solution.

Embodiment 272. The method of embodiment 271, wherein the excipient that modulates viscosity, turbidity or both viscosity and turbidity is an excipient according to any preceeding embodiment.

Embodiment 273. A method of reducing both the viscosity and the turbidity of an antisense oligonucleotide solution, said method comprising adding an effective amount of an excipient that modulates viscosity, turbidity or both to the antisense oligonucleotide solution.

Embodiment 274. The method of embodiment 273, wherein the excipient that modulates viscosity, turbidity or both viscosity and turbidity is an excipient according to any preceeding embodiment.

Embodiment 275. A method of increasing the viscosity, turbidity, or both the viscosity and turbidity of an antisense oligonucleotide solution, comprising reducing or removing the amount of an excipient that modulates viscosity, turbidity or both from the antisense oligonucleotide solution.

BRIEF DESCRIPTION OF THE FIGURES

FIG. 3 illustrates the turbidity plotted over (approximate) temperature profile of 220 mg/mL ISIS NO. 426115

FIGS. 4A and 4B illustrate the effect of NTU of Formazin reference suspensions on visible turbidity. FIG. 4A These standards are 0 (visually clear), 20, 100, 1000, and 4000

(visually turbid) NTU, respectively. FIG. 4B These standards shown in 2 mL, 13 mm vials are 20, 10, and 0 (WFI control) NTU respectively.

DETAILED DESCRIPTION OF THE INVENTION

Figure 1:
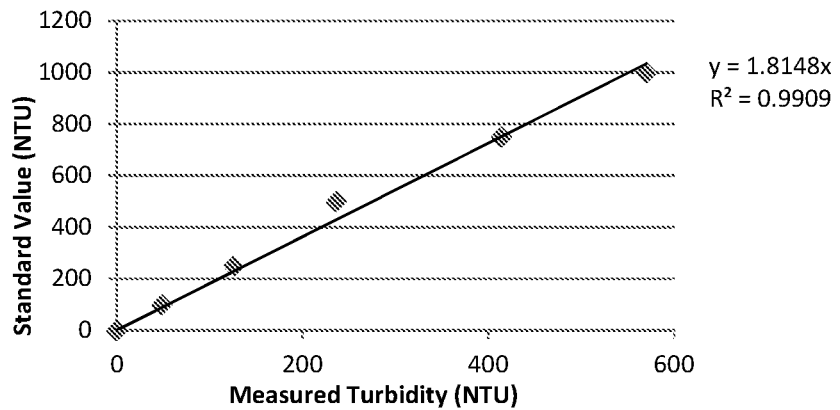
FIG. 1 illustrates a standard curve conversion for 13-mm sample tubes for 0-1000 NTU. CF for the tubes is shown to be the slope of the plot, which is 1.8148.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "aqueous solution" means a solution comprising one or more solutes in water. In certain embodiments, the water is sterile water. In certain embodiments, an aqueous solution is saline.

As used herein, "antisense oligonucleotide solution" means an aqueous solution comprising one or more antisense oligonucleotides. In certain embodiments, an antisense oligonucleotide solution comprises an aqueous solution having only one antisense oligonucleotide. In certain embodiments, an antisense oligonucleotide solution comprises an aqueous solution having more than one antisense oligonucleotide. In certain embodiments, an antisense oligonucleotide solution comprises an aqueous solution wherein an antisense oligonucleotide is present at a concentration between 0.1 and 500 mg/mL.

As used herein, "excipient" means any compound or composition other than water or an antisense oligonucleotide.

As used herein, "excipient that modulates viscosity, turbidity or both viscosity and turbidity" or "excipient that modulates viscosity, turbidity or both" means an excipient, the presence of which increases or decreases the viscosity and/or turbidity of an antisense oligonucleotide solution, compared to the viscosity or turbidity of the antisense oligonucleotide solution at the same concentration and temperature in the absence of the excipient.

As used herein, "aromatic compound" refers to a mono- or polycyclic carbocyclic ring system having one or more aromatic rings. Preferred aromatic ring systems have from about 5 to about 20 carbon atoms in one or more rings. Aromatic groups as used herein may optionally include further substituent groups.

The term "heterocyclic compound" as used herein, refers to a mono-, or poly-cyclic ring system that includes at least one heteroatom and is unsaturated, partially saturated, or fully saturated, thereby including heteroaryl groups and heterocyclic aromatic compounds. Heterocyclic compound is also meant to include fused ring systems wherein one or more of the fused rings contain at least one heteroatom and the other rings can contain one or more heteroatoms or optionally contain no heteroatoms. A heterocyclic compound typically includes at least one atom selected from sulfur, nitrogen or oxygen. In certain embodiments, a heterocyclic compound may include one or more rings, wherein each ring has one or more heteroatoms. In certain embodiments, a heterocyclic compound includes a monocyclic ring system with one or more heteroatoms. In certain embodiments, a heterocyclic compound includes a monocyclic ring system with two or more heteroatoms. Examples of heterocyclic compounds include, but are not limited to, [1,3] dioxolane, pyrrolidine, pyrazoline, pyrazolidine, imidazoline, imidazolidine, piperidine, piperazine, oxazolidine, isoxazolidine, morpholine, thiazolidine, isothiazolidine, quinoxaline, pyridazinone, tetrahydrofuran and the like. Heterocyclic compounds as used herein may optionally include further substituent groups.

As used herein, "heterocyclic aromatic compound" means any compound comprising a mono- or poly-cyclic aromatic ring system or fused ring system wherein at least one of the rings is aromatic and includes one or more heteroatoms. Heterocyclic aromatic compounds also include fused ring systems, including systems where one or more of the fused rings contain no heteroatoms. Heterocyclic aromatic compounds typically include one ring atom selected from sulfur, nitrogen or oxygen. Examples of heterocyclic aromatic compounds groups include without limitation, pyridine, pyrazine, pyrimidine, pyrrole, pyrazole, imidazole, thiazole, oxazole, isoxazole, thiadiazole, oxadiazole, thiophene, furan, quinoline, isoquinoline, benzimidazole, benzooxazole, quinoxaline and the like. Heterocyclic aromatic compounds can be attached to a parent molecule directly or through a linking moiety such as an aliphatic group or hetero atom. Heterocyclic aromatic compounds as used herein may optionally include further substituent groups.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyl comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2' bridge.

As used herein, "locked nucleic acid nucleoside" or "LNA" means a nucleoside comprising a bicyclic sugar moiety comprising a 4'-CH$_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonimidoyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C$_1$-C$_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N (Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, $O(CH_2)_2O(CH_2)_2N(CH_3)_2$, and N-substituted acetamide (O—$CH_2$—C(=O)—$N(R_m)$ $(R_n)$ where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—$N(CH_3)_2$, —$O(CH_2)_2O$ $(CH_2)_2N(CH_3)_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[$C(R_a)(R_b)$]$_n$—, —[$C(R_a)(R_b)$]$_n$—O—, —$C(R_aR_b$—)N(R)—O— or, —$C(R_aR_b)$—O—N(R)—; 4'-$CH_2$-2', 4'-$(CH_2)_2$-2', 4'-$(CH_2)_3$-2', 4'-$(CH_2)$—O-2' (LNA); 4'-$(CH_2)$—S-2'; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., J. Org. Chem., 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[$C(R_a)(R_b)$]$_n$—, —$C(R_a)$=$C(R_b)$—, —$C(R_a)$=N—, —C(=$NR_a$)—, —C(=O)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2—N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

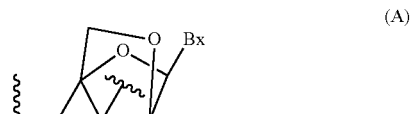

(A)

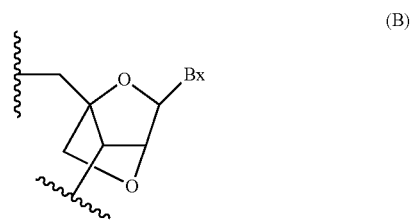

(B)

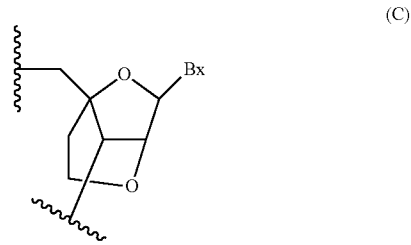

(C)

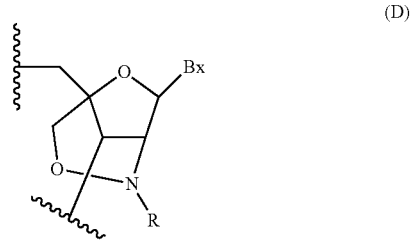

(D)

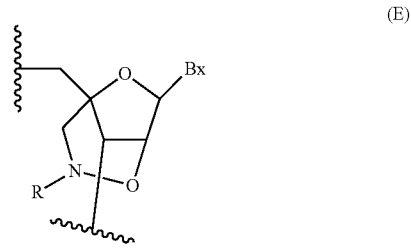

(E)

-continued

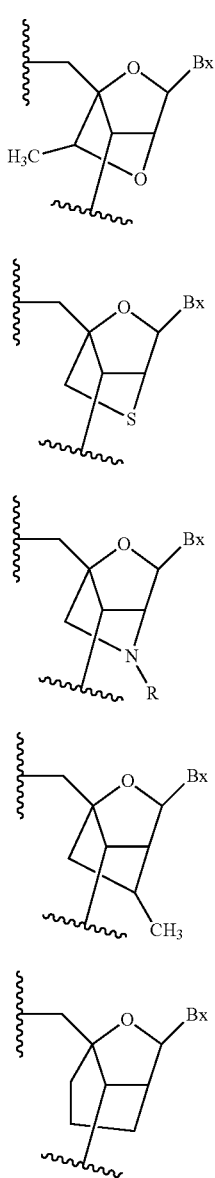

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

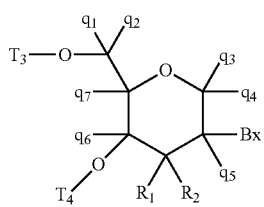

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

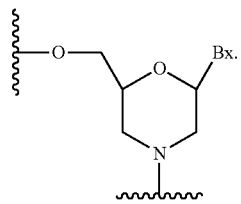

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'- dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

TABLE 1 below provides certain non-limiting examples of antisense compounds and their targets:

TABLE 1

Antisense Compounds

| Target | ISIS No | Indication | Sequence | Chemistry | SEQ ID NO |
|---|---|---|---|---|---|
| Factor XI | 416858 | Clotting disorder | ACGGCATTGGTGCACAGTTT | 5-10-5 MOE | 1 |
| TTR | 420915 | Amyloides | TCTTGGTTACATGAAATCCC | 5-10-5 MOE | 2 |
| Apo(a) | 494372 | CAD | TGCTCCGTTGGTGCTTGTTC | 5-10-5 MOE | 3 |
| Alpha1-antitrypsin | 487660 | Liver disease | CCAGCTCAACCCTTCTTTAA | 5-10-5 MOE | 4 |
| PTP-1B | 404173 | Diabetes | AATGGTTTATTCCATGGCCA | 5-10-5 MOE | 5 |
| GCGR | 449884 | Diabetes | GGTTCCCGAGGTGCCCA | 3-10-4 MOE | 6 |
| DGAT2 | 501861 | NASH | TCACAGAATTATCAGCAGTA | 5-10-5 MOE | 7 |
| Factor VII | 540175 | Cancer-associated thrombosis | GGACACCCACGCCCCC | 3-10-3 cEt/MOE | 8 |
| SMN | 396443 | SMA | TCACTTTCATAATGCTGG | Uniform MOE | 9 |
| FGFR4 | 463588 | Obesity | GCACACTCAGCAGGACCCCC | 5-10-5 MOE | 10 |
| apoB-100 | 301012 | High Cholesterol | GCCTCAGTCTGCTTCGCACC | 5-10-5 MOE | 11 |
| CRP | 329993 | CAD | AGCATAGTTAACGAGCTCCC | 5-10-5 MOE | 12 |
| ApoC-III | 304801 | High triglycerides | AGCTTCTTGTCCAGCTTTAT | 5-10-5 MOE | 13 |
| GCCR | 426115 | Diabetes | GCAGCCATGGTGATCAGGAG | 5-10-5 MOE | 14 |
| STAT3 | 481464 | Cancer | CTATTTGGATGTCAGC | 3-10-3 (S)-cEt | 15 |
| eIF-4E | 183750 | Cancer | TGTCATATTCCTGGATCCTT | 5-10-5 MOE | 16 |

TABLE 1-continued

Antisense Compounds

| Target | ISIS No | Indication | Sequence | Chemistry | SEQ ID NO |
|---|---|---|---|---|---|
| SOD1 | 333611 | ALS | CCGTCGCCCTTCAGCACGCA | 5-10-5 MOE | 17 |
| GHR | 227452 | Acromegaly | TCAGGGCATTCTTTCCATTC | 5-10-5 MOE | 18 |
| Clusterin | 112989 | Cancer | CAGCAGCAGAGTCTTCATCAT | 4-13-4 MOE | 19 |
| Hsp27 | 306053 | Cancer | GGGACGCGGCGCTCGGTCAT | 4-12-4 MOE | 20 |
| CMV | 2922 | Retinitis | GCGTTTGCTCTTCTTCTTGCG | Uniform deoxy | 21 |
| ICAM-1 | 2302 | Ulcerative colitis | GCCCAAGCTGGCATCCGTCA | Uniform deoxy | 22 |
| VLA-4 | 107248 | Multiple sclerosis | CTGAGTCTGTTTTCCATTCT | 3-9-8 MOE | 23 |
| CTGF | 412294 | Fibrosis | GTTTGACATGGCACAATGTT | 2-13-5 MOE | 24 |
| c-raf kinase | 13650 | Ocular disease | TCCCGCCTGTGACATGCATT | 6-8-6 MOE | 25 |

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, an antisense oligonucleotide modulates splicing of a pre-mRNA.

Certain Properties of Antisense Compounds

Viscosity

In certain embodiments, antisense oligonucleotide solutions possess varying degrees of viscosity, and the viscosity of antisense oligonucleotide solutions depends on many factors. Some factors include, but are not limited to, length, nucleobase sequence, nucleobase modifications, nucleobase modification motif, and/or sugar modification of the antisense oligonucleotide. In certain embodiments, the viscosity of an antisense oligonucleotide solution may be difficult to predict. In certain embodiments an antisense oligonucleotide solution may exhibit a relatively high viscosity, while an antisense oligonucleotide solution comprising a similar antisense oligonucleotide (partially homologous sequence, similar modifications, etc.) may exhibit a relatively low viscosity. In certain embodiments it may be desireable to lower the viscosity of a given antisense oligonucleotide solution, for example, in certain embodiments it may be desirable to to lower the viscosity of a given antisense oligonucleotide solution so that higher amounts of an antisense oligonucleotide may be present in a given volume of solution.

In certain embodiments it may be desirable to increase the viscosity of a given antisense oligonucleotide solution. In certain embodiments, viscosity may be increased or decreased depending on a variety of factors, e.g. concentration, volume of solute, temperature, and/or pH. In certain embodiments, the desireable viscosity varies. In certain embodiments it may be desirable to increase or decrease viscosity, depending on the particular route of delivery or application a given antisense oligonucleotide solution.

In certain embodiments, viscosity is often a concentration-limiting factor. While not wishing to be bound by theory, in certain embodiments, as the concentration of an antisense oligonucleotide is increased, interactions between antisense oligonucleotide molecules likewise increase. In certain embodiments, certain antisense oligonucleotides may interact to form aggregates which may increase viscosity and/or turbidity. Certain antisense oligonucleotides may interact to form antisense oligonucleotide polymers, which may increase viscosity and/or turbidity. In certain embodiments, as the concentration of an antisense oligonucleotide in solution increases, the viscosity of the antisense oligonucleotide solution also increases. In certain embodiments, it is undesirable to have an antisense oligonucleotide solution having a high viscosity. For example, if the viscosity of an antisense oligonucleotide solution is too high, then it may become difficult to manufacture an antisense oligonucleotide solution including but not limited to an antisense oligonucleotide solution drug product. As another example, if the viscosity of an antisense oligonucleotide solution is too high, filtration time during manufacturing may increase, adding time and cost to the manufacturing process. As another example, if the viscosity of an antisense oligonucleotide solution is too high, it may become more difficult to pre-fill syringes with accurate and precise amounts of the antisense oligonucleotide solution. As another example, if the viscosity of an antisense oligonucleotide solution is too high, it may become more difficult to administer to an animal, human, or patient. As another example, if the viscosity of an antisense oligonucleotide solution is too high, drug clearance from the subcutaneous injection site may be slowed. As another example, if the viscosity of an antisense oligonucleotide solution is too high, a larger gauge needle may be required to effectively administer doses of the antisense oligonucleotide solution, which may exacerbate discomfort upon injection. In certain embodiments, it is therefore desirable to have an antisense oligonucleotide solution having both a high concentration of antisense oligonucleotide and low viscosity.

In certain embodiments, if the viscosity of an antisense oligonucleotide solution is too high, then the concentration of the antisense oligonucleotide in solution may be reduced to reduce the viscosity of the antisense oligonucleotide solution to a desirable level. The reduction of the concentration of an antisense oligonucleotide in the antisense oligonucleotide solution may be undesirable for several reasons. For example, as the concentration of an antisense oligonucleotide in an antisense oligonucleotide solution is decreased, animals, humans, and/or patients must receive a larger volume of antisense oligonucleotide solution to receive the desired amount of an antisense oligonucleotide. In certain embodiments, it is therefore desirable to reduce the viscosity of an antisense oligonucleotide solution without reducing the concentration of the antisense oligonucleotide within the antisense oligonucleotide solution. In certain embodiments, it is therefore desirable to have an antisense oligonucleotide solution having both a high concentration of antisense oligonucleotide and low viscosity.

In certain embodiments, certain antisense oligonucleotide solutions having desirable concentrations of antisense oligonucleotides have undesirably high viscosities. In certain embodiments, the addition of one or more excipients that modulate viscosity, turbidity or both may reduce the viscosity of a certain antisense oligonucleotide solution to a desirable level.

In certain embodiments described herein, it is recognized that viscosity of an oligonucleotide solution may vary with temperature. In certain embodiments, the viscosity may be expressed as a range of cP units relative to a concentration of oligonucleotide in solution. For example, in certain embodiments, the viscosity of the antisense oligonucleotide solution is less than 40 cP when the concentration of the antisense oligonucleotide is between 40 to 60 mg/mL. In certain such embodiments, the viscocity of the solution and the concentration of the oligonucleotide represent an approximate measurement of viscocity and approximate concentration of oligonucleotide at a given temperature or range of temperatures. For example, in certain embodiments described herein, the temperature of the solution for which viscocity is measured is about 25 degrees Celsius.

In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 40 to 60 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 45 to 55 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 80 to 120 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 90 to 110 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 140 to 160 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 165 to 185 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 180 to 220 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 190 to 210 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 210 to 230 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 230 to 260 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 245 to 255 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 260 to 300 mg/mL. In certain embodiments, the addition of one or more excipients that modulate viscosity, turbidity or both to the antisense oligonucleotide solution reduces the viscosity of the antisense oligonucleotide solution to less than 40 cP when the concentration of the antisense oligonucleotide is between 300 to 400 mg/mL.

In certain embodiments, the addition of one or more excipients that modulate viscosity, turbidity or both to the antisense oligonucleotide solution reduces the viscosity of the antisense oligonucleotide solution to less than 40 cP when the antisense oligonucleotide has one or more modified sugars having 2'-MOE modifications. In certain embodiments, the addition of one or more excipients that modulate viscosity, turbidity or both to the antisense oligonucleotide solution reduces the viscosity of the antisense oligonucleotide solution to less than 40 cP when the antisense oligonucleotide has one or more modified sugars having 2'-OMe modifications. In certain embodiments, the addition of one or more excipients that modulate viscosity, turbidity or both to the antisense oligonucleotide solution reduces the viscosity of the antisense oligonucleotide solution to less than 40 cP when the antisense oligonucleotide has one or more modified sugars having 2'-F modifications. In certain embodiments, the addition of one or more excipients that modulate viscosity, turbidity or both to the antisense oligonucleotide solution reduces the viscosity of the antisense oligonucleotide solution to less than 40 cP when the antisense oligonucleotide has one or more modified sugars having LNA modifications. In certain embodiments, the addition of one or more excipients that modulate viscosity, turbidity or both to the antisense oligonucleotide solution reduces the viscosity of the antisense oligonucleotide solution to less than 40 cP when the antisense oligonucleotide has one or more modified sugars having cEt modifications.

Turbidity

While not wishing to be bound by theory, the presence of turbidity in antisense oligonucleotide solutions is associated with the formation of antisense oligonucleotide strand aggregates. In certain embodiments, the presence of turbidity in antisense oligonucleotide solutions makes the antisense oligonucleotide solution appear white and cloudy. In certain embodiments, the presence of turbidity in antisense oligonucleotide solutions makes the antisense oligonucleotide solution appear to contain small particles. In certain embodiments, it is desirable to have antisense oligonucleotide solutions that have low turbidity. In certain embodiments, it is desirable to have antisense oligonucleotide solutions that appear clear and particle-free when viewed by the naked eye. In certain embodiments, it is desirable to have antisense oligonucleotide solutions that have turbidity below 20 NTU.

In certain embodiments, turbidiy may be induced via a freeze-thaw method, wherein an antisense oligonucleotide solution is frozen and then rapidly thawed, as described herein. In certain embodiments, the freese-thaw method induces turbidity wherein a given antisense oligonucleotide solution would not normally demonstrate turbidity, or wherein a given antisense oligonucleotide solution would demonstrate turbidity after a long period of time. In certain embodiments turbidity represents an aesthetic problem, but does not affect the efficacy or safety of a given antisense oligonucleotide solution.

In certain embodiments, certain antisense oligonucleotide solutions having desirable concentrations of antisense oligonucleotides have undesirably high turbidity. In certain embodiments, certain antisense oligonucleotide solutions having desirable concentrations of antisense oligonucleotides have undesirably high turbidity wherein the antisense oligonucleotide solution has a cloudy or milky white appearance. In certain embodiments, certain antisense oligonucleotide solutions having desirable concentrations of antisense oligonucleotides have undesirably high turbidity wherein the antisense oligonucleotide solution appears to have small amounts of particulate interspersed throughout the antisense oligonucleotide solution. In certain embodiments, the addition of one or more excipients that modulate viscosity, turbidity or both may reduce the turbidity of a certain antisense oligonucleotide solution to a desirable level. In certain embodiments, the addition of one or more excipients that modulate viscosity, turbidity or both may reduce the turbidity of a certain antisense oligonucleotide solution from having a cloudy appearance to a having a clear appearance to the naked eye. In certain embodiments, the addition of one or more excipients that modulate viscosity, turbidity or both may reduce the turbidity of a certain antisense oligonucleotide solution from having a milky white appearance to a having a clear appearance to the naked eye. In certain embodiments, the addition of one or more excipients that modulate viscosity, turbidity or both may reduce the turbidity of a certain antisense oligonucleotide solution from visible particles to a having a clear particle-free appearance to the naked eye.

In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 40 to 60 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 45 to 55 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 80 to 120 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 90 to 110 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 140 to 160 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 165 to 185 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 180 to 220 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 190 to 210 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 210 to 230 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 230 to 260 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 245 to 255 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 260 to 300 mg/mL. In certain embodiments, the addition of one or more excipients that modulate viscosity, turbidity or both to the antisense oligonucleotide solution reduces the turbidity of the antisense oligonucleotide solution to less than 20 NTU when the concentration of the antisense oligonucleotide is between 300 to 400 mg/mL.

In certain embodiments, the addition of one or more excipients that modulate viscosity, turbidity or both to the antisense oligonucleotide solution reduces the turbidity of the antisense oligonucleotide solution to less than 20 NTU when the antisense oligonucleotide has one or more modified sugars having 2'-MOE modifications. In certain embodiments, the addition of one or more excipients that modulate viscosity, turbidity or both to the antisense oligonucleotide solution reduces the turbidity of the antisense oligonucleotide solution to less than 20 NTU when the antisense oligonucleotide has one or more modified sugars having 2'-OMe modifications. In certain embodiments, the addition of one or more excipients that modulate viscosity, turbidity or both to the antisense oligonucleotide solution reduces the turbidity of the antisense oligonucleotide solution to less than 20 NTU when the antisense oligonucleotide has one or more modified sugars having 2'-F modifications. In certain embodiments, the addition of one or more excipients that modulate viscosity, turbidity or both to the antisense oligonucleotide solution reduces the turbidity of the antisense oligonucleotide solution to less than 20 NTU when the antisense oligonucleotide has one or more modified sugars having LNA modifications. In certain embodiments, the addition of one or more excipients that modulate viscosity, turbidity or both to the antisense oligonucleotide solution reduces the turbidity of the antisense oligonucleotide solution to less than 20 NTU when the antisense oligonucleotide has one or more modified sugars having cEt modifications.

Osmolarity

While not wishing to be bound by theory, antisense oligonucleotide solutions possess varying concentrations of osmolarity, and the osmolarity of antisense oligonucleotide solutions depends on many factors. Some factors include but are not limited to, length, nucleobase sequence, nucleobase modifications, nucleobase modification motif, and/or sugar modification of the antisense oligonucleotide. In certain embodiments, the osmolarity of an antisense oligonucleotide solution may be difficult to predict. In certain embodiments an antisense oligonucleotide solution may exhibit a relatively high concentrations of osmolarity, while a similar antisense oligonucleotide solution may exhibit a relatively low concentrations of osmolarity.

In certain embodiments, certain antisense oligonucleotide solutions having desirable concentrations of antisense oligonucleotides have undesirably low osmolarity, and are hypotonic. In certain embodiments, it is undesirable to have an antisense oligonucleotide solution having low osmolarity, and hypotonicity. For example, if the osmoloarity of an antisense oligonucleotide solution is too low, then an animal, human, or patient may experience pain at the injection site. In certain embodiments, it is therefore desirable to increase the osmolarity of an antisense oligonucleotide solution. In certain embodiments, it is therefore desirable to have the antisense oligonucleotide solution become isotonic.

In certain embodiments, the addition of one or more excipients that modulate viscosity, turbidity or both to the antisense oligonucleotide solution increases the osmolarity of the antisense oligonucleotide solution. In certain embodiments, the addition of one or more excipients that modulate viscosity, turbidity or both to the antisense oligonucleotide solution increases the osmolarity of the antisense oligonucleotide solution wherein the antisense oligonucleotide solution becomes isotonic.

pH

While not wishing to be bound by theory, antisense oligonucleotide solutions possess varying pH levels, and the pH levels of antisense oligonucleotide solutions depends on many factors. Some factors include, but are not limited to length, nucleobase sequence, nucleobase modifications, nucleobase modification motif, and/or sugar modification of the antisense oligonucleotide. In certain embodiments, the pH of an antisense oligonucleotide solution may be difficult to predict. In certain embodiments an antisense oligonucleotide solution may exhibit a relatively high pH, while an antisense oligonucleotide solution of a similar antisense oligonucleotide may exhibit a relatively low pH.

In certain embodiments, the addition of one or more excipients that modulate viscosity, turbidity or both to the antisense oligonucleotide solution alters the pH of the antisense oligonucleotide solution. In certain embodiments, the addition of one or more excipients that modulate viscosity, turbidity or both to the antisense oligonucleotide solution increases pH of the antisense oligonucleotide solution. In certain embodiments, the addition of one or more excipients that modulate viscosity, turbidity or both to the antisense oligonucleotide solution decreases pH of the antisense oligonucleotide solution. In certain embodiments, the addition of one or more excipients that modulate viscosity, turbidity or both to the antisense oligonucleotide solution buffers pH of the antisense oligonucleotide solution. In certain embodiments, the addition of one or more excipients that modulate viscosity, turbidity or both to the antisense oligonucleotide solution buffers the pH of the antisense oligonucleotide solution around a pH of 8.0. (e.g., 7.8 to 8.2) In certain embodiments, the addition of one or more excipients that modulate viscosity, turbidity or both to the antisense oligonucleotide solution buffers the pH of the antisense oligonucleotide solution around a pH of 7.4. (e.g., 7.2-7.6) In certain embodiments, the addition of one or more excipients that modulate viscosity, turbidity or both to the antisense oligonucleotide solution buffers the pH of the antisense oligonucleotide solution around a pH of 7.0. (e.g. 6.8-7.2).

Antimicrobial

In certain embodiments it is desirable to include an antimicrobial agent to an antisense oligonucleotide solution to facilitate storage or delivery. In certain embodiments it is not necessary to include an antimicrobial agent to an antisense oligonucleotide solution to facilitate storage or delivery of the antisense oligonucleotide solution. In certain embodiments an antimicrobial agent is added to an antisense oligonucleotide solution. In certain embodiments no antimicrobial agents are added to an antisense oligonucleotide solution. In certain embodiments antisense oligonucleotide solutions are prepared without antimicrobial agents. In certain embodiments one or more excipients that modulate viscosity, turbidity or both may also serve as an antimicrobial agent or preservative. In certain embodiments one or more excipients that modulate viscosity, turbidity or both may not have any antimicrobial or preservative properties.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

Certain Excipients

As reported in scientific or patent literature, some oligonucleotide compounds form aggregates when in solution and aggregation may causes undesired viscosity, turbidity, or both. In certain embodiments, oligonucleotide solutions having high viscosity are undesirable because it complicates delivery through a syringe. For example, oligonucleotide solutions having high viscosity may only effectively get delivered using a high gauge needle which may cause excess pain or discomfort to a patient. In certain embodiments, oligonucleotide solutions having high turbidity are undesirable because the oligonucleotide solution may appear to have one or more impurities present.

In certain embodiments, oligonucleotide solutions having additives can mitigate only turbidity or only viscosity (see US 20110098343). In certain embodiments, this disclosure provides that both turbidity and viscosity can be comitigated by a single excipient, for example, L-tryptophan, pyridoxine, L-Phenylalanine, and nicotinamide. In certain embodiments, additional excipients that have potential to mitigate both turbidity and viscosity include but are not limited to thymine, adenine, riboflavin, thiamine, and tryptamine. In certain embodiments, effective excipients have heterocyclic character and/or an ability to act as a hydrogen bond donor and/or a hydrogen bond acceptor. In certain embodiments, excipients with nonaromatic rings may not be effective for viscosity reduction.

In certain embodiments, certain properties of effective excipients, e.g. (i) aromatic homocyclicity or heterocyclicity and (ii) the ability to act as a hydrogen bond donor and/or acceptor, may be consolidated into one excipient or compound. In certain embodiments, two or more excipients may together possess one or more properties of effective excipients. For example, in certain embodiments, a first excipient may be an aromatic homocyclic or heterocyclic compound but may not have the ability to act as a hydrogen bond donor and/or acceptor. In certain such embodiments, a second excipient may have the ability to act as a hydrogen bond donor and/or acceptor, but may not be an aromatic homocyclic or heterocyclic compound. In certain such embodiments, the first excipient may act as a aromatic homocyclic or heterocyclic compound and a second excipient may act as a hydrogen bond donor and/or acceptor and the combination of the first and second excipient may produce an effective excipient for mitigating turbidity, viscocity, or both. In certain embodiments, a mixture of two or more excipients, the sum of which contain (i) aromatic homocyclicity or heterocyclicity and (ii) the ability to act as a hydrogen bond donor and/or acceptor, are effective in mitigating both turbidity and viscosity.

In certain embodiments, antisense oligonucleotide compositions provided herein comprise one or more modified antisense oligonucleotides and one or more excipients. Any suitable excipient known to those having skill in the art may be used. For example, suitable excipients may be found in, for example "Handbook of Pharmaceutical Excipients," American Pharmaceutical Association Publications, Washington D.C., $6^{th}$ Edition, 2009; which is hereby incorporated herein by reference in its entirety. In certain such embodiments, excipients are selected from salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, excipients are selected from Adenine, Benzyl Alcohol, m-Cresol, Cytidine, Cytidine Monophosphate, Cytosine, Dextran, Guanine Monophosphate, D-Mannitol, Methylparaben, Nicotinamide, Phenol, 2-Phenoxyethanol, L-Phenylalanine, Pyridoxine, Sodium Chloride, Thymine, tryptophan, L-Tryptophan, L-Tyrosine, Ascorbic Acid, Benzamide, o-Benzenediol, Benzenehexol, L-Histidine, Hydroxypyridine, Indole, D-Mannitol+Phenol mixture, D-Mannitol+Pyridine mixture, 2H-Pyran, Pyrazinamide, Pyridine, Pyrimidine, 2-Pyrone, Riboflavin, Thiamine, Tryptamine, ethanol, (2-Hydroxypropyl)-β-cyclodextrin, Niacin, Polyethylene Glycol 600, Polyethylene Glycol 4600, Propylene Glycol, Pyridoxine, Sucrose, Thymidine, Tween 80, Uridine, Thymine, caffeine, acridine orange, ethidium bromide, propidium iodide, cyanine dyes such as PicoGreen®, thiamine hydrochloride, ethylene diamine tetraacetic acid, and 1,2-dihydroxybenzene.

In certain embodiments, excipients comprise heterocyclic molecules. In certain embodiments, excipients comprise heterocyclic amines. In certain embodiments, excipients comprise aromatic molecules or molecules having one one or more aromatic ring. In certain embodiments, excipients comprise heterocyclic molecules wherein the heteroatom is oxygen. In certain embodiments, excipients comprise heterocyclic molecules wherein the heteroatom is nitrogen. In certain embodiments, excipients comprise heterocyclic molecules wherein the heteroatom is sulfur.

In certain embodiments, the excipient lowers the viscosity of an antisense oligonucleotide composition. In certain embodiments, the excipient lowers the turbidity of an antisense oligonucleotide composition. In certain embodiments, the excipient increases the osmolarity of an antisense oligonucleotide composition. In certain embodiments, the excipient decreases the osmolarity of an antisense oligonucleotide composition. In certain embodiments, the excipient increases the pH of an antisense oligonucleotide composition. In certain embodiments, the excipient decreases the pH of an antisense oligonucleotide composition. In certain embodiments, the excipient buffers the pH of an antisense oligonucleotide composition. In certain embodiments, the excipient lowers the turbidity and the viscosity of an antisense oligonucleotide composition. In certain embodiments, the excipient lowers the turbidity and the viscosity of an antisense oligonucleotide composition and also increases the osmolarity of the antisense composition. In certain embodiments, the excipient lowers the turbidity and the viscosity of an antisense oligonucleotide composition and also decreases the osmolarity of the antisense composition.

In certain embodiments, a mixture of two or more excipients lowers the viscosity of an antisense oligonucleotide composition. In certain embodiments, a mixture of two or more excipients lowers the turbidity of an antisense oligonucleotide composition. In certain embodiments, a mixture of two or more excipients increases the osmolarity of an antisense oligonucleotide composition. In certain embodiments, a mixture of two or more excipients decreases the osmolarity of an antisense oligonucleotide composition. In certain embodiments, a mixture of two or more excipients increases the pH of an antisense oligonucleotide composition. In certain embodiments, a mixture of two or more excipients decreases the pH of an antisense oligonucleotide composition. In certain embodiments, a mixture of two or more excipients buffers the pH of an antisense oligonucleotide composition. In certain embodiments, a mixture of two or more excipients lowers the turbidity and the viscosity of an antisense oligonucleotide composition. In certain embodiments, a mixture of two or more excipients lowers the turbidity and the viscosity of an antisense oligonucleotide composition and also increases the osmolarity of the antisense composition. In certain embodiments, a mixture of two or more excipients lowers the turbidity and the viscosity of an antisense oligonucleotide composition and also decreases the osmolarity of the antisense composition.

In certain embodiments, one or more excipients may effective reduce the viscosity, turbidity, or both the viscocity and turbidity of a solution of one or more modified antisense oligonucleotides. In certain embodiments, one or more excipients may effective reduce the viscocity, turbidity, or both the viscocity and turbidity of a solution of one or more modified antisense oligonucleotides but this excipient may, for example, increase the osmolality of the solution to an undesirable amount. In certain embodiments, In certain embodiments, salts such as NaCl, KCl, LiCl, $MgCl_2$, or $CaCl_2$ may used to modulate the osmolality of an oligonucleotide in solution, but may also induce the turbidity of certain oligonucleotides. In certain such embodiments, it may therefore be desireable to use an excipient selected from among L-Tryptophan, Niacinamide, L-Phenylalanine, and L-Histidine to modulate the osmolality of an oligonucleotide solution and to also modulate the viscosity and/or turbidity of the oligonucleotide solution. In certain such embodiments, it may therefore be desireable to use an excipient selected from among L-Tryptophan, Niacinamide, L-Phenylalanine, and L-Histidine to increase the osmolality of an oligonucleotide solution and to also decrease the viscosity of the oligonucleotide solution. In certain such embodiments, it may therefore be desireable to use an excipient selected from among L-Tryptophan, Niacinamide, L-Phenylalanine, and L-Histidine to increase the osmolality of an oligonucleotide solution and to also decrease the turbidity of the oligonucleotide solution. In certain such embodiments, it may therefore be desireable to use an excipient selected from among L-Tryptophan, Niacinamide, L-Phenylalanine, and L-Histidine to increase the osmolality of an oligonucleotide solution and to also decrease the viscosity and decrease the turbidity of the oligonucleotide solution.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

General Method for Evaluating Turbidity, and Viscosity

The general method for measuring turbidity is as follows. Turbidity qualitative assessment is performed by visually inspecting control and sample vials that have frozen at −20° C. and subsequently thawed at 5° C. Their appearance is noted before the samples equilibrate to room temperature. These results are often documented with photographs. Turbidity quantitative measurement is performed on a Hach 2100 AN Laboratory Turbidimeter and is used to test turbidity of 3.2-3.4 mL of solution filled in a 13-mm glass tube. Typically the solution has received freeze-thaw treatment similar to the one described above to induce turbidity formation prior to measurement. The instrument is standardized with Formazin reference suspensions over a range of Nephelometric Turbidity Units (NTUs) that brackets the turbidity of the samples being tested.

Viscosity qualitative assessment is performed by visually inspecting the flow of a sample solution in a container and comparing it to a control. In this case, sample viscosities were noted as increased or decreased only when an obvious difference was noted (e.g., if at 5° C. the control sample appeared to mimic honey in viscosity, the viscosity of excipient samples appearing as free-flowing liquids are noted as "decreased", while excipient samples appearing as solid gel are noted as "increased"). Quantitative viscosity measurement comprises of two forms, dynamic and kinematic. The form relating to antisense oligonucleotide (ASO) drug product characterization is dynamic viscosity. Two instruments that are currently used in the Pharmaceutical Development (PD) laboratory to measure dynamic viscosity are RheoSense m-VROC viscometer and Malvern Instruments Bohlin CVO 100 rheometer. Further information about the instruments can be obtained from the manufacturer's websites (rheosense.com and malvern.com/CVO).

RheoSense m-VROC System

The RheoSense m-VROC utilizes a microelectromechanical systems (MEMS) chip which consists of three silicone pressure sensor arrays embedded lengthwise along the center of a rectangular channel. The liquid sample is loaded into a syringe pump, which dispenses the sample into the microfluidic chip at a specified flow rate. The pressure drop over distance of a flowing test liquid is measured, and it is expected to be linear for Newtonian fluids if a fully developed flow is ensured within the channel. The shear stress and viscosity are calculated according to fluid dynamic principles.

There are four classifications of chips available for the RheoSense m-VROC, labeled A, B, C, and D. They vary consecutively in size, with the A chip having the smallest inner channel dimensions that enables precise measurements of low viscosity samples, while the D chip is built for high viscosity samples. Within each chip category there are also three channel depths: 20, 50, and 100 μm, indicated as the "02", "05", and "10" series. The maximum recommended sample viscosities for use with each chip are shown in Table 2.

TABLE 2

Recommended upper viscosity limits for each Rheosense m-VROC chip

| Chip | Maximum Recommended Viscosity (cP) |
|---|---|
| A | 100 |
| B | 400 |
| C | 3,000 |
| D | 10,000 |

Malvern Instruments Bohlin CVO 100 System

The Bohlin CVO 100 operates via a bob-and-cup mechanism, whereby the torque required to accelerate a bob in a cup filled with sample fluid to a specified angular speed is measured and converted mathematically to viscosity. A single interface is used for all sample types evaluated in, with the bob and cup being removable for sample loading and cleaning. The instrument specifications are shown in Table 3.

TABLE 3

Instrument Specifications for Bohlin CVO 100 System

| | |
|---|---|
| Method Description | Shear ramp method with a spinning bob rheometer and no inertial corrections |
| Cell | 1 mL Mooney-Ewart |
| Gap | 75 microns |
| Temperature | Isothermal, typically at 25° C., 15° C., or 5° C. |

TABLE 3-continued

Instrument Specifications for Bohlin CVO 100 System

| | |
|---|---|
| Standard and Sample Volume | 1.2 mL |
| Standards | 10, 50, and 100 cP polydimethylsiloxane viscosity reference fluids |
| Model Fit | Newtonian |

Example 1a

General Method for Evaluating Osmolality

Osmolality is measured using Wescor VAPRO 5600 Vapor Pressure Osmometer. A small paper disc is loaded onto the sampling area, and 10 uL of test solution is dispensed into the disc. Calibration is performed using 100, 290, and 1000 mOsm/kg standards. Further information about this instrument can be obtained from the manufacturer's website (wescor.com/biomedical/osmometer/vapro5600.html).

Wescor VAPRO 5600 Vapor Pressure Osmometer

VAPRO 5600 osmometer measures a test solution's dew point temperature depression, which is related to its vapor pressure. Vapor pressure is a colligative property of a solution which linearly correlates to the concentration of particles dissolved in the solvent (i.e. osmolality). The particle's size, density, configuration, or electrical charge has no bearing on a colligative property. Increasing osmolality decreases the solution vapor pressure.

In the VAPRO system, an internal thermocouple hygrometer joins with the sample holder when the sample has been loaded to form a small chamber enclosing the sample disc. After the chamber temperature has equilibrated, the thermocouple is cooled, thus inducing dew formation on the thermocouple surface. The thermocouple is then heated until it reaches the dew point. The difference between ambient temperature and the dew point temperature is the dew point temperature depression. The instrument processes this result and provides a reading in mmol/kg, equaling mOsm/kg. (Note: mOsm/kg refers to the concentration of dissociated molecules in solution. Therefore, 1 mmol/L NaCl yields 2 mmol/L of dissociated ions; i.e. $Na^+$ and $Cl^-$, which equals 2 mOsm/L. Applying the density conversion of 1 kg/L yields 2 mOsm/kg). The instrument specifications are shown in Table 3a.

TABLE 3a

Instrument Specifications for Wescor VAPRO 5600

| | |
|---|---|
| Sample Volume | 10 μL |
| Measurement Range | 20-300 mmol/kg |
| Measurement Time | 90 seconds |
| Resolution | 1 mmol/kg |
| Calibration | Opti-mole ™ osmolality standards |

Example 2

General Method Used to Screen Excipients for the Mitigation of Turbidity and Viscosity Turbidity Screening The screening of the excipients for mitigating turbidity is performed by adding 0.1 to 5% (w/v) of the excipient at pH 7-8 to a solution of ASO in water at a concentration of 200 mg/mL to 250 mg/mL. After the solution is prepared, a 1 mL sample is aliquoted and filled into a 2-mL clean glass vial, stoppered, sealed, frozen at −20° C., and thawed at 5° C. The sample is then evaluated for turbidity with the turbidimeter or more commonly by visual inspection. The results from visual inspection is converted to a score from 0 to 3 with 0 being visually clear (i.e., <20 NTU); 1 being less turbid than a control but not clear; 2 approximately the same turbidity as a control; and 3 being more turbid than a control. A solution of ASO in water is used as the control.

The excipients investigated for mitigation of turbidity are independently selected from but are not limited to adenine, benzyl alcohol, m-cresol, cytidine, cytidine monophosphate, cytosine, dextran, guanine monophosphate, D-mannitol, methylparaben, nicotinamide, phenol, 2-phenoxyethanol, L-phenylalanine, pyridoxine, sodium chloride, thymine, L-tryptophan, L-tyrosine, ascorbic acid, benzamide, o-benzenediol, benzenehexol, caffeine, L-histidine, hydroxypyridine, indole, 2H-pyran, pyrazinamide, pyridine, pyrimidine, 2-pyrone, riboflavin, thiamine, thiamine hydrochloride, 1,2-dihydroxybenzene (catechol), ethylene diamine tetraacetic acid (EDTA), tryptamine, calcium folinate, sodium folinate (vitamin B9), D-mannitol and phenol mixture, D-mannitol and pyridine mixture, D-mannitol and niacinamide (nicotinamide) mixture, L-phenylalanine and pyridoxine mixture, pyridoxine and benzyl alcohol mixture, L-phenylalanine and L-histidine mixture; any mixture combination of L-phenylalanine, L-tryptophan, L-histidine, and niacinamide; and dinucleotides or trinucleotides or other shortmer oligonucleotide probes; and nucleic acid stains such as acridine orange, ethidium bromide, propidium iodide, and cyanine dyes such as PicoGreen®.

Viscosity Screening

A concentrated stock solution of ASO in water is diluted using solid excipient or a concentrated stock solution of excipient. A typical dilution is from a concentration of 250 to 200 mg/mL of ASO at pH 8. Viscosity would either be visually noted, or measured using the RheoSense m-VROC viscometer or Malvern Instruments Bohlin CVO 100 rheometer as described in Example 1. The measured results for viscosity are then obtained and normalized to the results when the diluent is only water with no excipient present.

The excipients investigated for mitigation of viscosity are independently selected from but are not limited to benzyl alcohol, m-cresol, cytidine, cytosine, dextran, ethanol, (2-Hydroxypropyl)-β-cyclodextrin, D-mannitol, niacin, nicotinamide, polyethylene glycol 600 (PEG$_{600}$), polyethylene glycol 4600 (PEG$_{4600}$), propylene glycol, pyridoxine, sodium chloride, sucrose, thymidine, L-tryptophan, uridine, adenine, thymine, Tween 80, cytidine monophosphate, guanine monophosphate, methylparaben, phenol, 2-phenoxyethanol, L-phenylalanine, L-tyrosine, ascorbic acid, benzamide, o-benzenediol, benzenehexol, caffeine, L-histidine, hydroxypyridine, indole, 2H-pyran, pyrazinamide, pyridine, pyrimidine, 2-pyrone, riboflavin, thiamine, tryptamine, thiamine hydrochloride, 1,2-dihydroxybenzene (catechol), ethylene diamine tetraacetic acid (EDTA), calcium folinate, sodium folinate (vitamin B9), D-mannitol and phenol mixture, D-mannitol and pyridine mixture, D-mannitol and phenol mixture, D-mannitol and pyridine mixture, D-mannitol and niacinamide (nicotinamide) mixture, L-phenylalanine and pyridoxine mixture, pyridoxine and benzyl alcohol mixture, L-phenylalanine and L-histidine mixture; any mixture combination of L-phenylalanine, L-tryptophan, L-histidine, and niacinamide; and dinucleotides or trinucleotides or other shortmer oligonucleotide probes; and nucleic acid stains such as acridine orange, ethidium bromide, propidium iodide, and cyanine dyes such as PicoGreen®.

Note: Not all the aforementioned excipients are viable for formulation. Some are used in the screening simply for mechanistic studies.

Example 3

Turbidity and Viscosity Evaluation for ISIS NO. 426115

Antisense oligonucleotide Isis No. 426115 was selected for turbidity and viscosity evaluation. The ASO and its motif are described in Table 4. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. An "N" indicates a U, T, C, $^{me}$C, G or A nucleoside.

TABLE 4

Antisense Oligonucleotide Isis No. 426115
Selected for Turbidity and Viscosity Evaluation

| Isis No. | Composition (5' to 3') | Motif | SEQ ID No. |
|---|---|---|---|
| 426115 | N$_e$N$_e$N$_e$N$_e$N$_e$NNNNNNNNNNNN$_e$N$_e$N$_e$N$_e$N$_e$ | 5-10-5 | 14 |

Turbidity Evaluation for ISIS NO. 426115

Several excipients in Example 2 were selected and screened for their effect in mitigating the turbidity of ISIS NO. 426115. The turbidity experiment was performed in the same manner as described in Example 2. To an aqueous solution of ISIS NO. 426115 at a concentration of 220 mg/mL, the excipient was added at the percentage (%, w/v) as indicated in Table 5. The solution was frozen at −20° C., thawed to 5° C. and subjected to turbidity evaluation. Turbidity was analyzed and compared to a control by visual inspection using a scoring format of 0 to 3 with 0 being visually clear; 1 being less turbid than a control but not clear; 2 approximately the same turbidity as a control; and 3 being more turbid than a control. A solution of ISIS NO. 426115 at a concentration of 220 mg/mL at pH 7-8 in only water was used as the control. The results are presented in Table 5.

As illustrated, several excipients when used individually or in combination with other excipients at various concentrations demonstrated desirable reduction in turbidity with a score of 1 or lower as compared to the control.

TABLE 5

Effect of various excipients on turbidity
for ISIS NO. 426115 at 220 mg/mL at 5° C.

| Excipient | Excipient concentration (%, w/v) | Turbidity (visual inspection) |
|---|---|---|
| Adenine | 0.5 | 0 |
| Ascorbic acid | 0.5 | 2 |
| Benzyl alcohol | 0.5 | 2 |
| | 1.5 | 0 |
| Caffeine | 0.5 | 0 |
| | 1.5 | 0 |
| m-Cresol | 0.3 | 3 |
| Cytidine | 0.01 | 2 |
| | 0.2 | |
| | 0.5 | |
| | 5.0 | 0 |
| Cytidine Monophosphate | 0.5 | 2 |
| Cytosine | 0.005 | 2 |
| | 0.2 | 2 |
| | 0.5 | 0 |
| | 1.0 | |
| Dextran | 0.5 | 2 |
| 1,2-Dihydroxybenzene (catechol) | 0.5 | 3 |
| Ethylene diamine tetraacetic acid (EDTA) | 0.2 | 2 |
| | 1.0 | 3 |
| Guanine Monophosphate | 0.5 | 2 |
| L-Histidine | 1.5 | 0 |
| | 2.0 | 0 |
| Hydroxypyridine or 2 Pyridone | 0.5 | 1 |
| | 1.0 | 0 |
| D-Mannitol (0.5) + Phenol (0.5) mixture | 1.0 (total) | 2 |

TABLE 5-continued

Effect of various excipients on turbidity
for ISIS NO. 426115 at 220 mg/mL at 5° C.

| Excipient | Excipient concentration (%, w/v) | Turbidity (visual inspection) |
|---|---|---|
| D-Mannitol (0.5) + Pyridine (0.5) mixture | 1.0 (total) | 1 |
| D-Mannitol (0.5) + Niacinamide (0.5) mixture | 1.0 (total) | 1 |
| D-Mannitol | 2.0 | 2 |
|  | 5.0 |  |
|  | 10 |  |
|  | 15 |  |
| Methylparaben | 0.2 | 3 |
|  | 0.5 | 2 |
|  | 1.5* | 0 |
| *excipient saturated and precipitated |  |  |
| Nicotinamide or Niacinamide | 0.5 | 2 |
|  | 1.0 | 1 |
|  | 1.5 | 0 |
|  | 2.0 |  |
|  | 2.5 |  |
|  | 3.0 |  |
|  | 5.0 |  |
| Phenol | 0.5 | 3 |
| 2-Phenoxyethanol | 0.5 | 3 |
| L-Phenylalanine | 0.5 | 1 |
|  | 1.5 | 0 |
| Pyrazinamide | 0.5 | 1 |
|  | 1.0 | 0 |
| Pyridine | 0.5 | 2 |
| Pyridoxine | 1.0 | 2 |
|  | 1.5 |  |
| Sodium Chloride | 0.5 | 2 |
| Thiamine HCl | 1 | 0 |
| Thymine | 0.5 | 0 |
| L-Tryptophan | 0.1 | 2 |
|  | 0.2 |  |
|  | 0.3 |  |
|  | 0.4 | 1 |
|  | 0.5 | 0 |
|  | 1.5 | 0 |
| L-Tyrosine | 0.04 | 2 |
| Calcium Folinate | 0.5 | 2 |
| L-Histidine | 0.5 | 2 |
|  | 1.5 | 1 |
|  | 2 | 0 |
| Indole | 0.1 | 2 |
| 2H-Pyran | 0.5 | 2 |
| Pyrimidine | 0.5 | 2 |
| 2-Pyrone | 0.5 | 1 |
| Riboflavin (Vitamin B2) | 0.025 | 2 |
| D-Mannitol (0.5) + Nicotinamide/Niacinamide (0.5) mixture | 1 (total) | 1 |
| L-phenylalanine (1) + Pyridoxine (0.5) | 1.5 (total) | 0 |
| Pyridoxine (0.5) + Benzyl alcohol (0.5) | 1 (total) | 0 |

Viscosity Evaluation for ISIS NO. 426115

Several excipients in Example 2 were selected and screened for their effect in mitigating the viscosity of ISIS NO. 426115. The viscosity experiment was performed in the same manner as described in Example 2. A concentrated stock solution of ASO in water was diluted using solid excipient or a concentrated stock solution of excipient. The dilution was at a concentration of 220 mg/mL of ISIS NO. 426115 at pH 7-8. Viscosity at 25° C. and 5° C. was measured using the RheoSense m-VROC viscometer as described in Example 1. The results for viscosity were obtained and normalized to the results of the control when the diluent was only water. Normalized viscosity was calculated by dividing the viscosity of the excipient present vs the viscosity of the control. The results are presented in Table 6.

As illustrated, at 25° C. or 5° C., several excipients when used alone or in combination with other excepients at various concentrations demonstrated desirable reduction in the viscosity with a normalized viscosity below 1.00.

TABLE 6

Effect of various excipients on viscosity of
ISIS NO. 426115 at 220 mg/mL at 25° C. and 5 ° C.

| Excipient | Excipient Conc. (%, w/v) | Viscosity (cP) 25° C. | Viscosity (cP) 5° C. | Normalized Viscosity* 25° C. | Normalized Viscosity* 5° C. |
|---|---|---|---|---|---|
| None (Control) | 0 | 79 | 28,500 | 1.00 | 1.00 |
| L-Tryptophan | 0.5 | 73 | 12,000 | 0.9 | 0.4 |
|  | 1.5 | 64 | 7,758 | 0.8 | 0.3 |
| Nicotinamide (Niacinamide) | 1.5 | 50 | 3,000 | 0.6 | 0.1 |
| Phenylalanine | 1.5 | 41 | 1,604 | 0.5 | 0.1 |
| Thiamine HCl | 1 | 95 | 79,000 | 1.2 | 2.8 |
| Pyridoxine HCl (0.5%) + benzyl alcohol (0.5%) | 1 | 106 | 19,000 | 1.3 | 0.7 |
| Pyridoxine HCl (0.5%) + phenylalanine (1%) | 1.5 | 46 | 2,539 | 0.6 | 0.1 |
| Caffeine | 1.5 | 148 | 35,000 | 1.9 | 1.2 |
| Histidine | 0.5 | 73 | NT | 0.9 | NT |
|  | 1.5 | 63 | NT | 0.8 | NT |
|  | 2 | 47 | 4,759 | 0.6 | 0.2 |
| Pyrazinamide | 1 | 59 | NT | 0.7 | NT |
| Methylparaben | 1.5 | 120 | NT | 1.5 | NT |

*Normalized to ISIS NO. 426115 at concentration of 220 mg/mL in water
NT = Not Tested As reported in scientific or patent literature, some additives can mitigate only turbidity or only viscosity (see US 20110098343). Unlike the literature, results from Tables 4 and 5 demonstrated that both turbidity and viscosity can be comitigated by a single excipient such as L-tryptophan, benzyl alcohol, L-histidine, L-phenylalanine, and nicotinamide. In certain embodiments, additional excipients that have potential to mitigate both turbidity and viscosity based on our current study include but are not limited to thymine, adenine, riboflavin, thiamine, and tryptamine since, in certain embodiments, several effective excipients have aromatic character (with heterocylicity enhancing their turbidity mitigation property) and an ability to act as a hydrogen bond donor and/or a hydrogen bond acceptor.

Osmolality Measurement

The osmolality of some samples from the screenings above was measured and compared to the control using the procedure illustrated in Example 1a. The results are presented in Table 6a, below.

The molar increase in solution osmolality compared to the control was expected to equal the molar amount of excipient added, since no ionic dissociation was expected. For example, adding 73.4 mmol/kg of L-Tryptophan (which equals to 73.4 mOsm/kg assuming the density is 1 kg/L) to a control solution of 431 mOsm/kg, the expected increase in osmolality of the solution would be 73.4 mOsm/kg (which equals to 504.4 mOsm/kg total solution osmolality). As illustrated in Table 6a, both L-tryptophan and niacinamide showed an increase in osmolality less than expected at 26 mOsm/kg, and 66 mOsm/kg rather than at 73.4 mOsm/kg and 122.8 mOsm/kg, respectively compared to the control. Phenylalanine showed an increase in osmolality as expected, while histidine showed an increase in osmolality more than expected at 119 mOsm/kg.

TABLE 6a

Effect of various excipients on osmolality for ISIS 426115 at 220 mg/mL

| Excipient | Excipient Conc. (%, w/v) | Excipient Conc. (mmol/kg)* | Expected Osmolality (mOsm/kg) | Measured Osmolality (mOsm/kg) | Expected Osmolality Increase (mOsm/kg) | Measured Osmolality Increase (mOsm/kg) |
|---|---|---|---|---|---|---|
| Control | 0 | 0.0 | 431 | 431 | 0 | 0 |
| L-Tryptophan | 1.5 | 73.4 | 504.4 | 457 | 73.4 | 26 |
| Niacinamide | 1.5 | 122.8 | 553.8 | 497 | 122.8 | 66 |
| L-Phenylalanine | 1.5 | 90.8 | 521.8 | 522 | 90.8 | 91 |
| L-Histidine | 1.5 | 96.7 | 527.7 | 550 | 96.7 | 119 |

*assuming density = 1 kg/L

Example 4

Evaluation of Properties of Effective Turbidity and Viscosity Comitigator Excipients for ISIS NO. 426115

The properties of excipients which can effectively comitigate turbidity and viscosity of ISIS NO. 426115 were investigated. Several excipients in Example 2 were selected and screened using the same method as described previously. The properties that were examined included, but not limited to aromaticity, homocyclic vs. heterocyclic aromatic rings, and the number of hydrogen bond donor and/or acceptor.

The ASO samples were prepared in the same manner as described in Example 3. To an aqueous solution of ISIS NO. 426115 at a concentration of 220 mg/mL, the excipient was added at the percentage (%, w/v) as indicated in Table 7. The solution was frozen at −20° C., thawed to 5° C. and subjected to turbidity and viscosity evaluation. Turbidity and viscosity were analyzed and compared to a control by visual inspection. For turbidity evaluation, a scoring format of 0 to 3 was employed with 0 being visually clear; 1 being less turbid than a control but not clear; 2 approximately the same turbidity as a control; and 3 being more turbid than a control. A solution of ISIS NO. 426115 at a concentration of 220 mg/mL at pH 8 in only water was used as the control. The results are presented in Table 7.

As illustrated, ascorbic acid reduced turbidity but not viscosity compared to the control, while L-phenylalanine was able to reduce both turbidity and viscosity. Similarly, pyrazinamide was effective for co-mitigation at 0.5% (w/v). Benzamide was effective for mitigating turbidity but not for viscosity at 2% (w/v), while nicotinamide was able to co-mitigate turbidity and viscosity at the same concentration. Phenol was unable to mitigate turbidity and viscosity, while hydroxypyridine was able to co-mitigate. Thus, in certain embodiments, heterocyclicity with increasing number of non-carbon substituents such as nitrogen and oxygen, seem to improve turbidity reduction.

Both phenol and catechol were ineffective in reducing turbidity at 0.5% (w/v). Phenol appeared to increase viscosity while catechol had no effect. Pyridine was ineffective for both turbidity and viscosity reduction, while hydroxypyridine was effective for co-mitigation. These results suggest that excipients with more hydrogen bond donors and/or acceptors can be effective at turbidity and viscosity co-mitigation.

In certain embodiments, some excipients effective at decreasing turbidity and/or viscosity have heterocyclic or homocyclic aromatic character. In certain embodiments, some excipients effective at decreasing turbidity and/or viscosity are heterocyclic and nonaromatic, for example, ascorbic acid as shown in Table 7.

The results from Table 7 suggest that in certain embodiments, excipients that have heterocyclic aromatic or non-aromatic character and contain hydrogen-bond donor(s) and/or hydrogen-bond acceptor(s) mitigate both turbidity and viscosity.

In certain embodiments, the properties given in this example are consistent with single excipients that are effective at mitigating both turbidity and viscosity, for example, compounds that resemble nucleobases, and heterocyclic compounds that possess both hydrogen bond donors and acceptors. In certain embodiments, aromatic ring character appears to provide a benefit based on the planar nature that facilitates: (i) positioning hydrogen bonds at a low energy state and (ii) interference of base stacking.

TABLE 7

Effect of excipients in mitigating turbidity and viscosity of ISIS NO. 426115

| Chemical Structure | Excipient | Concentration (%, w/v) | Turbidity (visual inspection) | Viscosity Compared to Control (visual inspection) |
|---|---|---|---|---|
| 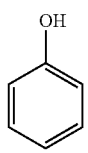 | Phenol | 0.5 | 3 | Increased |

TABLE 7-continued

Effect of excipients in mitigating turbidity and viscosity of ISIS NO. 426115

| Chemical Structure | Excipient | Concentration (%, w/v) | Turbidity (visual inspection) | Viscosity Compared to Control (visual inspection) |
|---|---|---|---|---|
| 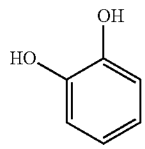 | Catechol (1,2-Dihydroxybenzene) | 0.5 | 3 | No notable difference |
| 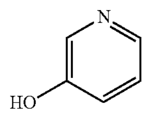 | Hydroxypyridine | 0.5 | 1 | Decreased |
| 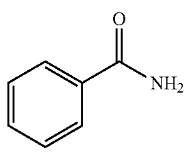 | Benzamide | 2 | 3 | Decreased |
| 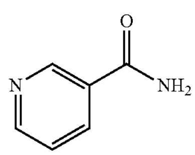 | Nicotinamide | 0.5 | 2 | No notable difference |
| | | 2 | 0 | Decreased |
| 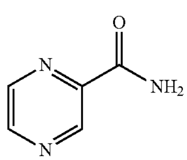 | Pyrazinamide | 0.5 | 1 | Decreased |
| 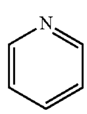 | Pyridine | 0.5 | 2 | No notable difference |
| 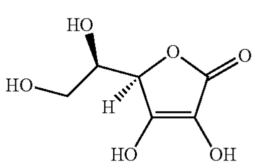 [SMILES: O=C1O[C@H]([C@H](O)CO)C(O)=C1O] | Ascorbic acid | 0.5 | 0 | No notable difference |
| 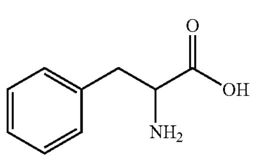 [SMILES: NC(Cc1ccccc1)C(=O)O] | Phenylalanine | 0.5 | 1 | Slightly decreased |

Example 5

Effect of Combining Singly Ineffective Excipients for Co-Mitigation of ISIS NO. 426115

The effect of combining excipients which are ineffective by themselves at mitigating both turbidity and viscosity of ISIS NO. 426115 was investigated. Several excipients in Example 2 were selected and screened using the same method as described previously. The ASO samples were prepared in the same manner as described in Example 3. To an aqueous solution of ISIS NO. 426115 at a concentration of 220 mg/mL at pH 8 the excipient mixture was added at the percentage (%, w/v) indicated in Table 8. The solution was frozen at −20° C., thawed to 5° C. and subjected to turbidity and viscosity evaluation. Turbidity and viscosity were analyzed and compared to a control by visual inspection. For turbidity evaluation, a scoring format of 0 to 3 was employed with 0 being visually clear; 1 being less turbid than a control but not clear; 2 approximately the same turbidity as a control; and 3 being more turbid than a control.

A solution of ISIS NO. 426115 at a concentration of 220 mg/mL at pH 8 in only water was used as the control. The results are presented in Table 8.

In certain embodiments, the chemical properties listed previously namely (i) aromatic homocyclicity or heterocyclicity and (ii) the ability to act as a hydrogen bond donor and/or acceptor do not have to be consolidated into one excipient or compound. In certain embodiments, it was discovered from our finding that a mixture of two excipients, which satisfies the two properties as a whole, can also be effective in mitigating both turbidity and viscosity. In certain embodiments, this was demonstrated by the mixture of 0.5% (w/v) mannitol and 0.5% (w/v) pyridine. Mannitol is a saturated linear carbon chain with hydroxyl groups, therefore possessing both hydrogen bond donors and acceptors; whereas pyridine is a heterocyclic aromatic compound lacking a hydrogen bond donor but has a hydrogen bond acceptor from its nitrogen atom. This mixture visually reduced both turbidity and viscosity compared to the control. In contrast, mannitol and pyridine by itself are ineffective at mitigating either turbidity or viscosity. In support of our observation for chemical properties of the excipients, it was found that mannitol and phenol mixture lacking a heterocyclic ring showed no significant mitigation in turbidity (Table 5).

The results from Table 8 suggest that in certain embodiments, other mixtures may potentially have such synergistic effects for both turbidity and viscosity mitigation as demonstrated by D-mannitol and pyridine mixture. Such mixtures include, but are not limited to, dextran and pyrimidine mixture or ascorbic acid and phenanthroline mixture.

eter; a StablCal Calibration Set for 2100AN Nephelometer, a StablCal Formazin Turbdity Standard at 1000 NTU; a VWR Precision 0.01° thermometer and Gerresheimer 13×100 mm glass culture tubes.

Method

A 4 mL sample of ISIS NO. 426115 at concentration of 220 mg/mL or 150 mg/mL was pipetted into a sample tube, capped and parafilmed at the cap joint. Both samples were allowed to freeze in a −20° C. storage and then moved to a 2-8° C. storage to thaw.

Turbidity Measurement

The turbidimeter was calibrated using Formazin turbidity calibration set. The 220 mg/mL sample from 2-8° C. storage was removed and allowed to stand at room temperature. The temperature of the sample was monitored until it reached approximately 13° C. or until condensation does not recur upon wiping of the tube surface and the temperature was recorded. The tube was then inserted in the nephelometer using a tube adaptor and turbidity measurement was taken every 2 minutes until turbidity value does not change by more than 0.1 NTU.

Temperature Profile

The 150 mg/mL sample from 2-8° C. storage was removed and allowed to stand at room temperature. The sample tube was inserted into the nephelometer (which does not need to be turned on). Condensation was not accounted for since it did not significantly affect the temperature profile. A temperature probe was inserted into the sample tube and the temperature was recorded over time.

Note: The temperature profiles of 150 mg/mL and 220 mg/mL samples of ISIS NO. 426115 has been shown to be identical in previous studies.

TABLE 8

Effect of excipient mixtures in mitigating turbidity and viscosity of ISIS NO. 426115

| Chemical Structure | Excipient | Concentration (%, w/v) | Turbidity (visual inspection) | Viscosity Compared to Control (visual inspection) |
| --- | --- | --- | --- | --- |
| 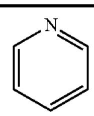 | Pyridine | 0.5 | 2 | No notable difference |
| 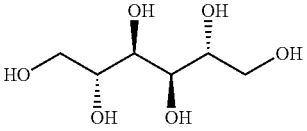 [SMILES: OC[C@@H](O)[C@@H](O)[C@H](O)[C@H](O)CO] | D-Mannitol | 2<br>5<br>10<br>15 | 2 | No notable difference |
| See boxes above | D-Mannitol + Pyridine | 0.5 + 0.5 | 1 | Decreased |

Example 6

Effect of Temperature and Time Dependency on ISIS NO. 426115 Turbidity

The effect of temperature and time dependency on the turbidity profile of freeze-thawed ISIS NO. 426115 at 220 mg/mL as it warmed up from 5° C. to room temperature was evaluated. The experiment was performed in the following manner.

Materials

The materials used to carry out the experiment included a solution of ISIS NO. 426115 in water at a concentration of 220 mg/mL and 150 mg/mL; a Hach 2100AN Nephelom- Sample Tube Turbidity Correction Factor (CF)

Since the 13-mm sample tubes used differ from the nephelometer's recommended set, a different path length of light applies for taking the sample turbidity. As such a CF was required to convert the readings into accurate NTU (Nephelometric Turbidity Units) values.

Formazin turbidity standards were volumetrically prepared by serial dilution of 1000 NTU standard using sterile water for injection. The standard values are 0, 100, 250, 500, 750 or 1000 NTU. The standard solutions were filled into 13-mm sample tubes and turbidity was measured. The standard values were plotted over measured turbidity values and a linear trend over the data points were fitted to obtain the slope. The slope is the CF for 13-mm sample tubes. The CF was used to convert measured values from 220 mg/mL ISIS NO. 426115 sample readings into actual NTU values.

Data Analysis and Results

The temperature and turbidity measurements over time were tabulated. The temperature profile was plotted by designating time zero to be at the same starting temperature as the turbidity sample. Overlaid the turbidity and temperature profiles over time and matched up the turbidity value with a temperature value along the time profile to generate an approximate turbidity vs temperature profile (FIG. 1).

Figure 2:
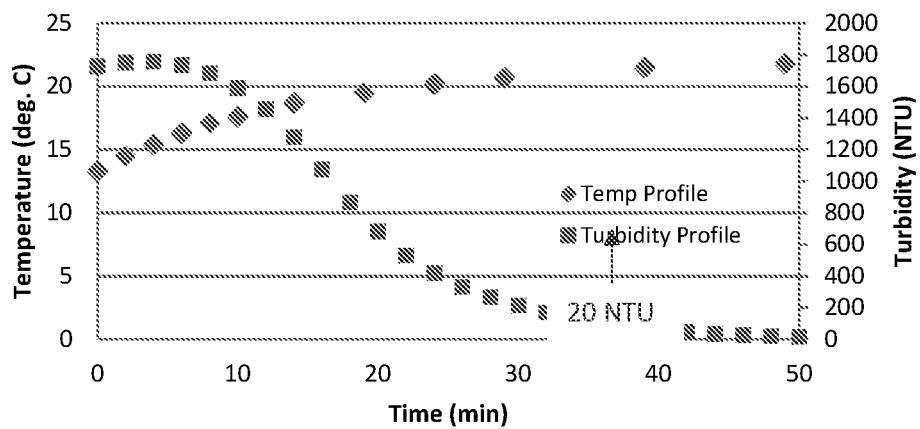
FIG. 2 illustrates the turbidity and temperature profiles of 220 mg/mL ISIS NO. 426115 over time. The turbidity reaches 20 NTU, which is approximately the lower limit of visible turbidity, at around 50 minutes.

The results showed that the CF for the tubes is the slope of the plot which is 1.8148 (FIG. 1). A decrease in turbidity appeared to lag behind the increase in temperature as shown in FIGS. 2 and 3. Turbidity remained at approximately 1800 NTU for the first 10 minutes when the temperature had increased by about 5 degrees. The solution temperature reached room temperature after approximately 30 minutes, however visually the turbidity did not completely dissipate until approximately 50 minutes, when it reached 20 NTU. FIG. 4 shows that 20 NTU is the approximate lower limit of visible turbidity in a solution.

In certain embodiments, this observation is indicative of a certain amount of thermal energy being required to break up the turbid species, which has been hypothesized to be self associated oligonucleotides. In addition, in certain embodiments, as shown in FIG. 3, there is an apparent melting temperature existing at approximately 19° C. At temperatures below that, the turbid species persist, and at temperatures above that they dissociate.

Example 7

Viscosity Evaluation for ISIS NO. 104838

Antisense oligonucleotide Isis No. 104838 was selected for viscosity evaluation. The ASO and its motif are described in Table 9. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. An "N" indicates a U, T, C, $^{me}$C, G or A nucleoside.

Several excipients in Example 2 were selected and screened for their effect in mitigating the viscosity of ISIS NO. 104838. The viscosity experiment was performed in the same manner as described in Example 2. A concentrated stock solution of ASO in water was diluted using solid excipient or a concentrated stock solution of excipient. The dilution was at a concentration of 200 mg/mL of ISIS NO. 104838 at pH 8. Viscosity at 25° C. was measured using the Malvern Instruments Bohlin CVO 100 rheometer as described in Example 1. The results for viscosity were obtained and normalized to the results of the control when the diluent was only water. The range of the control viscosity (105.1-113.6 cP) provided in Table 10 was generated from various independent studies and therefore, normalized viscosity was calculated based on the control value obtained from the same study. The results are shown below.

As illustrated, several excipients at various concentrations demonstrated a desirable reduction in viscosity with a normalized viscosity of below 1.00 as compared to the control.

TABLE 9

Antisense Oligonucleotide Isis No. 104838 Selected for Viscosity Evaluation

| Isis No. | Composition (5' to 3') | Motif | SEQ ID No. |
|---|---|---|---|
| 104838 | $N_eN_eN_eN_eN_e$NNNNNNNNNNN$N_eN_eN_eN_eN_e$ | 5-10-5 | 26 |

TABLE 10

Effect of various excipients on viscosity of ISIS NO. 104838 at 200 mg/mL at 25° C.

| Excipient | Excipient Conc. (%, w/v) | Viscosity (cP) | Normalized Viscosity* |
|---|---|---|---|
| None (control) | 0 | 105.1-113.6 | 1.00 |
| PEG$_{4600}$ | 5 | 194.8 | 1.85 |
| (2-Hydroxypropyl)-β-cyclodextrin | 5 | 178.2 | 1.60 |
| PEG$_{600}$ | 5 | 147.2 | 1.40 |
| Dextran 1500 | 5 | 130.9 | 1.18 |
| D-Mannitol | 5 | 115.5 | 1.10 |
| Sucrose | 5 | 122.1 | 1.10 |
| Niacin (Vitamin B$_3$) sodium salt | 5 | 123.8 | 1.09 |
| Tween 80 | 0.5 | 115.1 | 1.04 |
| Thymidine | 5 | 94.75 | 0.86 |
| Uridine | 5 | 89.05 | 0.81 |
| Cytosine | 1 | 81.89 | 0.74 |
| L-Tryptophan | 1.1 | 82.69 | 0.73 |
| Benzyl alcohol | 0.9 | 82.09 | 0.72 |
|  | 3.8 | 44.08 | 0.39 |
| Cytidine | 5 | 67.64 | 0.61 |
| m-Cresol | 2 | 62.40 | 0.55 |
| Nicotinamide/Niacinamide | 5 | 42.46 | 0.38 |

*Normalized to ISIS NO. 104838 concentration of 200 mg/mL in water

Example 8

Combining Singly Effective Excipients for Enhanced Turbidity and Viscosity Co-Mitigation of ISIS NO. 426115

The effect of combining effective excipients was evaluated for co-mitigation of turbidity and viscosity of ISIS NO. 426115 beyond what each excipient could perform individually. Tryptophan, niacinamide (nicotinamide), L-phenylalanine and L-histidine were selected for a factorial mixture design-of-experiment (DOE) study, where the total of all excipient mixture combinations equal 60 mM. The ratios are presented in Table 11, below.

Stock solutions of 220 mg/mL ISIS NO. 426115 containing 60 mM single excipients were prepared by adding solid ASO and excipient powders, diluting with water, and then pH-adjusting to target pH 7-8 as necessary. Subsequently, the stock solutions were combined in relevant ratios to total 1 mL solutions, and filled into 2-mL clean glass vials which were stoppered and sealed, to produce all 24 samples. Control solution of 220 mg/mL ISIS NO. 426115 without excipient was prepared separately using similar method. These samples were frozen and thawed in two cycles, by first freezing at −20° C. and thawing at 5° C., and then the process was repeated. Turbidity was analyzed after the two freeze-thaw cycles and compared to the control by visual inspection. A scoring format of 0 to 2 was employed with 0 being visually clear; 0.5 being very slightly turbid, 1 being slightly turbid; and 2 being as turbid as the control. Viscosity was measured at 25° C. using the Rheosense m-VROC system as described in Example 1. The results for viscosity were obtained and normalized to the results of the control when the diluent was only water. The results presented in Table 11 were then entered into a DOE software (Design-Expert®8) to determine statistical significance of the data and render a response surface showing the most ideal mixture for viscosity reduction.

As illustrated, all combinations of excipients at the ratios tested mitigated turbidity with the score of 1 or lower and also mitigated viscosity to less than 65% of the control. Design-Expert ANOVA analysis determined that the results possess adequate signal-to-noise ratio, and could be used to generate statistically significant models. Additionally, a viscosity response surface generated by the software showed that 50/50 combination of L-phenylalanine and L-histidine proved most effective at lowering viscosity.

control solution was also prepared without osmolality adjusters.

The solutions were frozen at −20° C., thawed to 5° C. Turbidity was evaluated by visual inspection and noted as either "clear" or "turbid". The results are presented in Table 13, below.

As illustrated, only ISIS 442245 with NaCl solution became turbid after freeze-thaw. The solution containing mannitol remained clear, which suggests that mannitol or other sugars such as glucose, sucrose, or fructose, may likely be suitable for use as osmolality adjusters replacing NaCl for turbidity mitigation.

TABLE 11

Effect of excipient mixtures in mitigating turbidity and viscosity of ISIS NO. 426115 at 25° C.

| Sample Type | L-tryptophan (mM) | Nicotinamide (Niacinamide) (mM) | L-phenylalanine (mM) | L-histidine (mM) | Turbidity (visual inspection) | Viscosity (cP) | Normalized Viscosity |
|---|---|---|---|---|---|---|---|
| Control | 0 | 0 | 0 | 0 | 2 | 66.841* | 1.0 |
| Test Samples | 60 | 0 | 0 | 0 | 0 | 38.855 | 0.58 |
| | 0 | 60 | 0 | 0 | 0 | 35.254 | 0.53 |
| | 0 | 0 | 60 | 0 | 0 | 34.296 | 0.51 |
| | 0 | 0 | 0 | 60 | 1 | 34.863 | 0.52 |
| | 30 | 30 | 0 | 0 | 0 | 36 | 0.54 |
| | 30 | 0 | 30 | 0 | 0 | 33.306 | 0.50 |
| | 30 | 0 | 0 | 30 | 0 | 38.378 | 0.57 |
| | 0 | 30 | 30 | 0 | 0 | 35.216 | 0.53 |
| | 0 | 30 | 0 | 30 | 0.5 | 35.61 | 0.53 |
| | 0 | 0 | 30 | 30 | 0.5 | 29.147 | 0.44 |
| | 20 | 20 | 20 | 0 | 0 | 35.863 | 0.54 |
| | 20 | 20 | 0 | 20 | 0 | 36.114 | 0.54 |
| | 20 | 0 | 20 | 20 | 0 | 32.279 | 0.48 |
| | 0 | 20 | 20 | 20 | 0.5 | 32.829 | 0.49 |
| | 15 | 15 | 15 | 15 | 0 | 34.739 | 0.52 |
| | 38 | 8 | 8 | 8 | 0 | 37.625 | 0.56 |
| | 8 | 38 | 8 | 8 | 0 | 34.778 | 0.52 |
| | 8 | 8 | 38 | 8 | 0 | 26.026 | 0.39 |
| | 8 | 8 | 8 | 38 | 0.5 | 35.13 | 0.53 |
| | 60 | 0 | 0 | 0 | 0 | 41.662 | 0.62 |
| | 0 | 60 | 0 | 0 | 0 | 36.625 | 0.55 |
| | 0 | 0 | 60 | 0 | 0 | 34.082 | 0.51 |
| | 0 | 0 | 0 | 60 | 1 | 35.56 | 0.53 |
| | 30 | 30 | 0 | 0 | 0 | 37.494 | 0.56 |

*Measured by taking the average from three independent studies

Example 10

Turbidity Evaluation for ISIS 442245 in the Presence of Osmolality Adjusters

Another ASO sequence, ISIS 442245 was used for turbidity evaluation. ISIS 442245 and its motif are described in Table 12. The internucleoside linkages throughout each modified oligonucleotide are phosphorothioate linkages (P=S). Nucleosides without a subscript are β-D-2'-deoxyribonucleosides. Nucleosides followed by a subscript "g" indicate 3'-F-HNA modified nucleosides. An "N" indicates a U, T, C, $^{me}$C, G or A nucleoside.

Osmolality adjusters for ISIS 442245 formulated at low ASO concentration can comprise salts such as NaCl, or sugars such as mannitol, or other substances. The effect of adding 0.6% (w/v) NaCl to 55 mg/mL ISIS 442245 was compared to adding 0.4% (w/v) mannitol. A buffered aqueous solution of ISIS 442245 at a concentration of 55 mg/mL was prepared by adding solid drug substance powder to 5 mM phosphate buffer (pH 7-8). To this stock solution, either 0.4% (w/v) mannitol or 0.6% NaCl (w/v) was added. A

TABLE 12

Antisense Oligonucleotide Isis 442245 Selected for Turbidity Evaluation

| Isis No. | Composition (5' to 3') | Motif | SEQ ID No. |
|---|---|---|---|
| 442245 | $N_gN_g$NNNNNNNNNN$N_gN_g$ | 2-10-2 | 27 |

TABLE 13

Turbidity Evaluation of ISIS 442245 in the Presence or Absence of Osmolality Adjusters

| Samples (all buffered with 5 mM phosphate buffer, pH 7-8) | Osmolality (mOsm/kg) | Turbidity (visual inspection) |
|---|---|---|
| Control: 55 mg/mL 442245 | 274 | Clear |
| 55 mg/mL 442245 + 0.4% mannitol | 505 | Clear |
| 55 mg/mL 442245 + 0.6% NaCl | 488 | Turbid |

Example 11

Turbidity Evaluation for ISIS 442245 with Excipients

Excipients such as tryptophan, niacinamide (nicotinamide) and phenylalanine were selected and screened for their effect in mitigating the turbidity of ISIS 442245 formulated with 5 mM phosphate buffer (pH 7-8) and 0.6% NaCl. The turbidity experiment was performed in the same manner as described in Example 2. To an aqueous solution of ISIS 442245 at a concentration of 55 mg/mL the excipients were added at the percentage (%, w/v) indicated in Table 14. L-Tryptophan and L-Phenylalanine concentrations tested were limited by their solubility. The solutions were frozen at −20° C., thawed to 5° C. and subjected to turbidity evaluation. Turbidity was analyzed and compared to a control by visual inspection using a scoring format of 0 to 3 with 0 being visually clear; 1 being less turbid than a control but not clear; 2 approximately the same turbidity as a control; and 3 being more turbid than a control. A solution of ISIS 442245 at a concentration of 55 mg/mL with 5 mM phosphate buffer (pH 7-8) and 0.6% NaCl is used as the control. The results are presented in Table 14.

As illustrated, the control appeared to be a turbid gel at 5° C. L-phenylalanine was shown to be effective in co-mitigating turbidity and viscosity at approximately 200 mM when the solution was stored for several days in 5° C. Upon freeze-thaw, the saturated L-phenylalanine precipitated and therefore caused the solution to become more turbid than the control. L-Tryptophan was also effective at turbidity mitigation at 50 mM after freeze-thaw, and would likely be a successful co-mitigator if it had been more soluble. Further, niacinamide was shown to co-mitigate turbidity and viscosity successfully at 400 mM while remaining stable after freeze-thaw. The results demonstrate that these excipients can be effective at mitigating turbidity and/or viscosity and can be used as co-mitigators for oligonucleotide sequences other than the ones exemplified herein.

TABLE 14

Effect of various excipients on turbidity and viscosity of ISIS NO. 442245 at 55 mg/mL formulated with 5 mM buffer pH 7-8 and 0.6% NaCl

| Excipient | Excipient Conc. (% w/v) | Excipient Conc. (mM) | Turbidity after 3 days at 5° C. (visual inspection) | Turbidity after freeze-thaw (visual inspection) | Viscosity at 5° C. (visual inspection) | Viscosity at 5° C. (cP) |
|---|---|---|---|---|---|---|
| Control | 0 | 0 | 2 | 2 | N/A | See note** |
| Niacinamide | 4.9 | 400 | 0 | 0 | Decreased | 5 |
| L-Tryptophan | 1.0 | 50 | 2 | 1 | No notable difference | See note** |
| L-Phenylalanine | 3.3* | 200* | 0 | 3 | Decreased | 31 |
|  | 2.5 | 150 | 0 | 2 | Decreased | NT |

*Due to excipient saturation, some excipients precipitated at this concentration

**Viscosity traces were erratic, showing some maximum values above 100 cP and minima around 0 cP. This is likely due to inhomogeneous sample gelling.

NT = not tested

---

The invention claimed is:

1. A method of reducing the turbidity, viscosity, or both viscosity and turbidity of an antisense oligonucleotide solution, said method comprising adding at least one excipient to an antisense oligonucleotide solution having an antisense oligonucleotide present at a concentration of 100-500 mg/ml wherein the antisense oligonucleotide comprises a modified oligonucleotide comprising at least one modified nucleoside, and wherein the viscosity and/or turbidity of the antisense oligonucleotide solution containing the excipient(s) is less than the viscosity and/or turbidity of the antisense oligonucleotide solution that does not contain the excipient(s).

2. The method of claim 1, wherein at least one of the at least one excipient comprises an aromatic ring or a heterocyclic ring compound.

3. The method of claim 1, wherein at least one of the at least one excipient is selected from the group consisting of adenine, benzyl alcohol, m-Cresol, cytidine, cytidine monophosphate, cytosine, dextran, guanine monophosphate, Methylparaben, nicotinamide, Phenol, 2-Phenoxyethanol, L-phenylalanine, pyridoxine, Sodium Chloride, thymine, tryptophan, L-tryptophan, L-tyrosine, Ascorbic Acid, benzamide, o-Benzenediol, benzenehexol, L-histidine, hydroxypyridine, indole, D-Mannitol+Phenol mixture, D-Mannitol+Pyridine mixture, 2H-pyran, pyrazinamide, pyrimidine, 2-pyrone, riboflavin, thiamine, tryptamine, ethanol, (2-Hydroxypropyl)-β-cyclodextrin, Niacin, Polyethylene Glycol 600, Polyethylene Glycol 4600, Propylene Glycol, Sucrose, thymidine, Tween 80, uridine, caffeine, acridine orange, ethidium bromide, propidium iodide, a cyanine dye, thiamine hydrochloride, ethylene diamine tetraacetic acid, 1,2-dihydroxybenzene, 1,2-dihydroxybenzene (catechol), D-Mannitol+niacinamide mixture, calcium folinate, L-phenylalanine+pyridoxine mixture, pyridoxine+benzyl alcohol mixture, pyridoxine HCl+benzyl alcohol mixture, niacin sodium salt, dextran 1500, and pyridoxine HCl+phenylalanine mixture.

4. The method of claim 1, wherein at least one of the at least one excipient increases the osmolarity of the solution, increases the pH of the solution, decreases the pH of the solution, and/or buffers the pH of the solution.

5. The method of claim 1, wherein the antisense oligonucleotide solution comprises a conjugated antisense oligonucleotide compound.

6. The method of claim 1, wherein the antisense oligonucleotide has a dynamic viscosity of more than 40 cP at 25° C., and/or has a turbidity of more than 20 NTU, when mixed in water or saline solution and in the absence of the at least one excipient.

7. The method of claim 1, wherein the antisense oligonucleotide is present at a concentration of 100-220 mg/mL.

8. The method of claim 1, wherein the antisense oligonucleotide is present at a concentration of 140-220 mg/mL.

9. The method of claim 1, wherein the antisense oligonucleotide is present at a concentration of 160-220 mg/mL.

10. The method of claim 1, wherein at least one of the at least one excipient comprises a heterocyclic aromatic ring compound.

11. The method of claim 1, wherein at least one of the at least one excipient comprises a heterocyclic aromatic ring compound comprising a nitrogen atom.

12. The method of claim 1, wherein the at least one modified nucleoside comprises at least one modified sugar moiety.

13. The method of claim 12, wherein the at least one modified sugar moiety is a 2'-substituted sugar moiety.

14. The method of claim 13, wherein the 2'-substituent of the at least one 2'-substituted sugar moiety is each independently selected from among: 2'-OMe, 2'-F, and 2'-MOE.

15. The method of claim 12, wherein the at least one modified sugar moiety is a bicyclic sugar moiety.

16. The method of claim 15, wherein the at least one bicyclic sugar moiety is LNA or cEt.

17. The method of claim 1, wherein at least one of the at least one excipient is adenine, cytidine, cytidine monophosphate, cytosine, guanine monophosphate, nicotinamide, pyridoxine, thymine, L-histidine, hydroxypyridine, pyrazinamide, pyrimidine, thiamine, thymidine, uridine, caffeine, or thiamine hydrochloride.

18. The method of claim 1, wherein at least one of the at least one excipient is benzyl alcohol, m-Cresol, L-phenylalanine, L-tyrosine, benzamide, or benzenehexol.

19. The method of claim 1, wherein at least one of the at least one excipient is L-tryptophan, indole, riboflavin, tryptamine, or calcium folinate.

20. The method of claim 1, wherein at least one of the at least one excipient is 2H-pyran or 2-pyrone.

* * * * *